(12) United States Patent
Scott et al.

(10) Patent No.: US 6,284,944 B1
(45) Date of Patent: Sep. 4, 2001

(54) GENE-TARGETED NON-HUMAN MAMMAL WITH A HUMAN FAD PRESENILIN MUTATION AND GENERATIONAL OFFSPRING

(75) Inventors: Richard W. Scott; Andrew G. Reaume; Karen Dorfman, all of West Chester, PA (US)

(73) Assignee: Cephalon, Inc,, West Chester, PA (US)

( * ) Notice: Subject to any disclaimer, the term of this patent is extended or adjusted under 35 U.S.C. 154(b) by 0 days.

(21) Appl. No.: 09/041,185

(22) Filed: Mar. 10, 1998

Related U.S. Application Data
(60) Provisional application No. 60/057,069, filed on Aug. 29, 1997.

(51) Int. Cl.⁷ .............................. C12N 5/00; C12S 15/00
(52) U.S. Cl. .................................. 800/3; 800/12; 800/18; 435/455
(58) Field of Search .............................. 800/3, 4, 12, 18; 435/455

(56) References Cited

U.S. PATENT DOCUMENTS

| | | | |
|---|---|---|---|
| 4,959,317 | 9/1990 | Sauer | 435/172.3 |
| 5,877,399 | * 3/1999 | Hsiao et al. | 800/2 |
| 5,986,054 | * 11/1999 | St. George-Hyslop et al. | 530/350 |

FOREIGN PATENT DOCUMENTS

WO 96/34097 * 10/1996 (WO) ............................ C12N/15/00

OTHER PUBLICATIONS

Koike, K. et al. Expression of Hepatitis C Virus Envelope Proteins in Transgenic Mice. Journal of General Virology 76:3031–3038, 1995.*
Wasco, W. et al. Familial Alzheimer's Chromosome 14 Mutations. Nature Medicine 1(9):848, Sep. 1995.*
Lee, M.K. et al. Expression and Endoproteolytic Processing of Wild Type and FAD–Linked Mutant Presenilin 1 in Transgenic Mice. Molecular Biology of the Cell 7(Supplement):653A, 1996.*
Hammer, R.E. et al. Genetic Engineering of Mammalian Embryos. Journal of Animal Science 63:269–278, 1986.*
Ebert, K.M. A Moloney MLV–Rat Somatotropin Fusion Gene Produces Biologically Active Somatotropin in a Transgenic Pig. Molecular Endocrinology 2:277–283, 1988.*
Whitelaw et al., Transgenic Res., 1, 3–13, 1991.*
Wall, Theriogenology, 43, 57–68, 1996.*
Palmiter et al., Ann Rev. Genet 20, 465–499, 1986.*
Palmiter et al., PNAS, Vo. 88, pp. 478–482, 1991.*
Askew et al., "Site–Directed Point Mutations in Embryonic Stem Cells: a Gene–Targeting Tag–and–Exchange Strategy," Mol. Cell Biol., 1993, 13(7), 4115–4124.
Borchelt et al., "Familial Alzheimer's Disease–Linked Presenilin 1 Variants Elevate Aβ1–42/1–40 Ratio In Vitro and In Vivo," Neuron, 1996, 17, 1005–1013.
Capecchi, M.R., "The New Mouse Genetics: Altering the Genome by Gene Targeting," Trends Genet., 1989, 5(3), 70–76.
Cataldo et al., "Gene Expression and Cellular Content of Cathepsin D in Alzheimer's Disease Brain: Evidence for Early Up–Regulation of the Endosomal–Lysosomal System," Neuron, 1995, 14, 671–680.
Church et al., "Genomic sequencing," Proc. Natl. Acad. Sci., 1984, 81, 1991–1995.
Clark et al., "The structure of the presenilin 1 (S182) gene and identification of six novel mutations in early onset AD families," Nature Genet., 1995, 11, 219–222.
Doan et al., "Protein Topology of Presenilin 1," Neuron, 1996, 17, 1023–1030.
Dower et al., "High efficiency transformation of E.coli by high voltage electroporation," Nucl. Acids Res., 1988, 16(13), 6127–6145.
Duff et al., "Increased amyloid–β42(43) in brains of mice expressing mutant presenilin 1," Nature, 1996, 383, 710–713.
Fiering et al., "An "in–out" strategy using gene targeting and FLP recombinase for the functional dissection of complex DNA regulatory elements: Analysis of the β–globin locus control region," Proc. Natl. Acad. Sci. USA, 1993, 90, 8469–8473.
Gu et al., "Deletion of a DNA Polymerase β Gene Segment in T Cells Using Cell Type–Specific Gene Targeting," Science, 1994, 265, 103–106.
Gu et al., "Independent Control of Immunoglobulin Switch Recombination at Individual Switch Regions Evidenced through Cre–IoxP–Mediated Gene Targeting," Cell, 1993, 73, 1155–1164.
Haass, "Presenilins: Genes for Life and Death," Neuron, 1997, 18, 687–690.
Holmes et al., "A Rapid Boiling Method for the Preparation of Bacterial Plasmids," Anal. Biochem., 1981, 114, 193–197.
Kim et al., "Endoproteolytic Cleavage and Proteasomal Degradation of Presenilin 2 in Transfected Cells," J. Biol. Chem., 1997, 272(17), 11006–11010.
Koller et al., "Altering Genes in Animals by Gene Targeting," Ann. Rec. Immunol., 1992, 10, 705–730.
Kovacs et al., "Alzheimer–associated presenilins 1 and 2: Neuronal expression in brain and localization to intracellular membranes in mammalian cells," Nature Med., 1996, 2(2), 224–229.

(List continued on next page.)

Primary Examiner—Dave Nguyen
(74) Attorney, Agent, or Firm—Woodcock Washburn Kurtz Mackiewicz & Norris LLP

(57) ABSTRACT

This invention discloses a gene-targeted non-human mammal and generational offspring with respect to the gene encoding a mutant protein product of a mutated presenilin 1 gene (PS-1); more specifically, a gene-targeted mouse with respect to the gene sequence encoding the mutant protein product of PS-1 which has been mutated to contain the human P264L mutation. Methods for screening chemical compounds using such mammals are also disclosed.

10 Claims, 19 Drawing Sheets

OTHER PUBLICATIONS

Lee et al., "Hyperaccumulation of FAD–linked presenilin 1 variants in vivo," *Nature Med.*, 1997, 3(7), 756–760.

Levitan et al., "Assessment of normal and mutant human presenilin function in *Caenorhabditis elegans*," *Proc. Natl. Acad. Sci. USA*, 1996, 93, 14940–14944.

Levitan et al., "Facilitation of lin–12–mediated signalling by sel–12, a *Caenorhabditis elegans* S182 Alzheimer's disease gene," *Nature*, 1995, 377, 351–354.

Levy–Lahad et al., "Candidate Gene for the Chromosome 1 Familial Alzheimer's Disease Locus," *Science*, 1995, 269, 973–977.

Mullis et al., "[21] Specific Synthesis of DNA in vitro via a Polymerase–Catalyzed Chain Reaction," *Methods Enzymol.*, 1987, 155, 335–350.

Nagy et al., "Derivation of completely cell culture–derived mice from early–passage embryonic stem cells," *Proc. Natl. Acad. Sci.*, 1993, 90, 8424–8428.

Reaume et al., "Cardiac Malformation in Neonatal Mice Lacking Connexin43," *Science*, 1995, 267, 1831–1834.

Rogaev et al., "Familial Alzheimer's disease in kindreds with missense mutations in a gene on chromosome 1 related to the Alzheimer's disease type 3 gene," *Nature*, 1995, 376, 775–778.

Rubinstein et al., "Introduction of a point mutation into the mouse genome by homologous recombination in embryonic stem cells using a replacement type vector with a selectable marker," *Nucl. Acid Res.*, 1993, 21(11), 2613–2617.

Salehi et al., "Decreased Activity of Hippocampal Neurons in Alzheimer's Disease Is Not Related to the Presence of Neurofibrillary Tangles," *J. Neuropath. Exp. Neurol.*, 1995, 54(5), 704–709.

Sanger et al., "DNA sequencing with chain–terminating inhibitors," *Proc. Natl. Acad. Sci.*, 1977, 74(12), 5463–5467.

Scheuner et al., "Secreted amyloid β–protein similar to that in the senile plaques of Alzheimer's disease is increased in vivo by the presenilin 1 and 2 and APP mutations linked to familial Alzheimer's disease," *Nature Med.*, 1996, 2(8), 864–870.

Sherrington et al., "Cloning of a gene bearing missense mutations in early–onset familial Alzheimer's disease," *Nature*, 1995, 375, 754–760.

Siman et al., "Strategies to alter the progression of Alzheimer's disease," *Curr. Opin. Biotech.*, 1996, 7, 601–607.

Slunt et al., "Nucleotide sequence of the chromosome 14–encoded S182 cDNA and revised secondary structure prediction," *Amyloid—Int. J. Exp. Clin. Invest.*, 1995, 2, 188–190.

te Riele et al., "Highly efficient gene targeting in embryonic stem cells through homologous recombination with isogenic DNA constructs," *Proc. Natl. Acad. Sci. USA*, 1992, 89, 5128–5132.

Thinakaran et al., "Endoproteolysis of Presenilin 1 and Accumulation of Processed Derivatives in Vivo," *Neuron*, 1996, 17, 181–190.

Tybulewicz et al., "Neonatal Lethality and Lymphopenia in Mice with a Homozygous Disruption of the c–abl Proto–Oncogene," *Cell*, 1991, 65, 1153–1163.

Wang et al., "Glycosylation of microtubule–associated protein tau: An abnormal posttranslational modification in Alzheimer's disease," *Nature Med.*, 1996, 2(8), 871–875.

Wasco et al., "Familial Alzheimer's chromosome 14 mutations," *Nature Med.*, 1995, 1(9), 848.

Wong et al., "Presenilin 1 is required for Notch1 and DII1 expression in the paraxial mesoderm,"*Nature*, 1997, 387, 288–292.

Wood et al., "Non–injection methods for the production of embryonic stem cell–embryo chimaeras," *Nature*, 1993, 365, 87–89.

Wurst et al., "Production of targeted embryonic stem cell clones," in *Gene Targeting: A Practical Approach*, Joyner, A.L. (ed.), IRL Press, Oxford University Press, Oxford, England, 1993, Ch. 2, 33–61.

Hogan et al., in *Manipulating the Mouse Embryo: A Laboratory Manual*, Cold Spring Harbor Laboratory, Cold Spring Harbor, New York, 1986.

Maniatis et al., *Molecular Cloning—A Laboratory Manual*, 2nd edition, Cold Spring Harbor Press, 1989.

\* cited by examiner pPS1-XB1 Construction

Example of Restriction Mapping the 5' Arm of Homology pPS1-8-TV Construction

GENE-TARGETED NON-HUMAN MAMMAL WITH A HUMAN FAD PRESENILIN MUTATION AND GENERATIONAL OFFSPRING

This patent document claims priority based upon Ser. No. 60/057,069 filed Aug. 29, 1997.

FIELD OF THE INVENTION

This invention relates to gene-targeted, non-human mammals.

BACKGROUND OF THE INVENTION

Alzheimer's disease (AD) is an age-dependent neurodegenerative disorder that leads to profound behavioral changes and dementia. Hallmark pathologies include the atrophy of brain grey matter as a result of the massive loss of neurons and synapses, and protein deposition in the form of both intraneuronal neurofibrillary tangles and extracellular amyloid plaques within the brain parenchyma. In addition, affected areas of the AD brain exhibit a reactive gliosis that appears to be a response to brain injury. Surviving neurons from vulnerable populations in AD show signs of metabolic compromise as indicated by alterations in the cytoskeleton (Wang et al., Nature Med. 2: 871–875 (1996)), Golgi complex (Salehi et al., J. Neuropath. Exp. Neurol. 54: 704–709 (1995)) and the endosomal-lysosomal system (Cataldo et al., Neuron 14: 671–680 (1995)).

Approximately 10 to 30% of AD cases are inherited in an autosomal dominant fashion and are referred to as "familial Alzheimer's disease" or "FAD." Genetic linkage studies have revealed that FAD is heterogeneous and a majority of the cases have been linked to gene mutations on chromosomes 1, 14, 19, or 21 (reviewed in Siman and Scott, Curr. Opin. Biotech. 7: 601–607 (1996)). Importantly, these individuals have been shown to develop the classical symptomatological and pathological profiles of the disease confirming that the mutations are associated with the development of the disease rather than a related syndrome. The locus on chromosome 14 is associated with a significant fraction of FAD, and mutations at the locus have been mapped to a single-copy gene, termed "S182" or "presenilin 1" (PS-1), that encodes a 467 amino acid protein (Sherrington et al., Nature 375: 754–760 (1995); Clark et al. Nature Genet. 11: 219–222 (1995)). A closely related gene, "STM2" or "presenilin 2" (PS-2), located on chromosome 1, has been linked to two additional FAD kindreds including the descendants of German families from the Volga valley of Russia (Levy-Lahad et al., Science 269: 973–977 (1995); Rogaev et al., Nature 376: 775–778 (1995)). PS-1 and PS-2 share an overall 67% amino acid sequence homology, and primary structure analysis indicates they are integral membrane proteins with 6 to 8 trans-membrane domains (Slunt et al., Amyloid—Int. J Exp. Clin. Invest. 2: 188–190 (1995); Doan et al., Neuron 17: 1023–1030 (1996)). Much of the information on function of the presenilins stems from the identification of a presenilin homolog in C. elegans termed "SEL-12", a 6 to 8 trans-membrane protein that appears to participate in an intracellular signaling pathway mediated by the lin-12/glp-1/Notch family (Levitan and Greenwald, Nature 377: 351–354 (1995)). PS-1 and SEL-12 proteins share a 48% sequence homology and have similar membrane orientations. Importantly, both human PS-1 and PS-2 can completely rescue the mutant sel-12 phenotype in C. elegans, indicating a role for the presenilins in Notch signaling (Levitan et al., Proc. Natl. Acad. Sci. USA 93: 14940–14944 (1996)).

FAD linked to the presenilins is highly penetrant and the aggressive nature of the disease suggests that the mutant protein participates in a seminal pathway of AD pathology. To date, over thirty five FAD mutations have been identified in PS-1, and two FAD mutations have been found in PS-2. All of the FAD mutations occur in conserved positions between the two presenilin proteins, suggesting that they are affecting functionally or structurally important amino acid residues. Interestingly, many of the mutated amino acids are also conserved in SEL-12. All but one of the presenilin mutations are missense mutations and the exception results in an aberrant RNA splicing event that eliminates exon 10, creating an internally-deleted mutant protein (reviewed in Haas, Neuron 18: 687–690 (1997)). These latter points, along with the genetic dominance of the disease, argue that disease pathogenesis in the presenilin kindreds requires the production of a mutant presenilin protein having a novel and detrimental function, rather than the simple loss or reduction of normal presenilin levels. The mutations do appear to disrupt normal presenilin function however, because mutant presenilins are not able to rescue or fully rescue the sel-12 phenotype (Levitan et al., Proc. Natl. Acad. Sci. USA 93: 14940–14944 (1996)).

Expression profiles of the presenilins have been examined at a gross level but, so far, these analyses have yielded little information on the mechanism of disease pathogenesis. Both presenilin 1 and 2 are widely expressed in the CNS and peripheral tissues. In brain, expression is enriched in neurons but is apparent in both AD-vulnerable and resistant areas. Cellular localization studies indicate that the proteins accumulate primarily in the Golgi complex and endoplasmic reticulum but no significant alterations in expression levels or subcellular distribution have been attributed to the FAD mutations (Kovacs et al., Nature Med. 2: 224–229 (1996)).

The presenilin proteins are processed proteolytically through two intracellular pathways. Under normal conditions, accumulation of 30 kD N-terminal and 20 kD C-terminal proteolytic fragments occurs in absence of the full-length protein. This processing pathway is highly regulated and appears to be relatively slow, accounting for turnover of only a minor fraction of the full-length protein. The remaining fraction appears to be rapidly degraded in a second pathway by the proteasome (Thinakaran et al., Neuron 17: 181–190 (1996); Kim et al., J. Biol. Chem. 272: 11006–11010 (1997)). Proteolytic metabolism of PS-1 variants linked to FAD appears to be different, but the relevance of the change to pathogenesis is not known (Lee, et al., Nature Med 3: 756–760 (1997)).

One pathogenic role for the mutant presenilins in FAD appears to be related to effects on processing of the amyloid precursor protein (APP) and production of the $A\beta$ peptide, the primary proteinaceous component of the extracellular neuritic plaque in the AD brain. Elevated serum levels of the longer form of $A\beta$ ($A\beta 42$), considered to be the more pathogenic species of the $A\beta$ peptides, have been measured in patients bearing PS-1 and PS-2 mutations (Scheuner et al., Nature Med. 2: 864–870 (1996)). Furthermore, overexpression of mutant, but not wild-type, presenilins in cell culture or transgenic mice results in enhanced secretion or production of $A\beta 42$ relative to $A\beta 40$ (Borchelt et al., Neuron 17: 1005–1013 (1996)). The mechanism by which the mutant presenilins affect APP processing is not known, but these results do support a causative role of increased $A\beta 42$ production in the development of FAD. Importantly, it is possible that mutant presenilins influence other AD pathogenic processes as well, such as presumptive intracellular signaling and cell death pathways involved directly or indirectly in neuronal dysfunction and degeneration.

Genetically-engineered animals have been used extensively to examine the function of specific gene products in vivo and their role in the development of disease phenotypes. The genetic engineering of mice can be accomplished according to at least two distinct approaches: (1) a transgenic approach where an exogenous gene is randomly inserted into the host genome, and (2) a gene-targeting approach where a specific endogenous DNA sequence or gene is partially or completely removed or replaced by homologous recombination. The transgene of a transgenic organism is comprised generally of a DNA sequence encoding the protein sequence and a promoter that directs expression of the protein coding sequences. A transgenic organism expresses the transgene in addition to all normally-expressed native genes. The targeted gene of a gene-targeted animal, on the other hand, can be modified in one of two ways: (1) a functional form where a modified version of the targeted gene is expressed, or (2) a non-functional or "null" form where the targeted gene has been disrupted resulting in loss or reduction of expression. If the targeted gene is a single copy gene and the animal is homozygous at the targeted locus, then, depending on the type of modification, the animal either does not express the targeted gene or expresses only a modified version of the targeted gene in absence of the normal form.

Transgenic mice expressing native and mutant forms of the presenilin proteins have been described (Borchelt et al., Neuron 17: 1005–1013 (1996); Duffet al., Nature 383: 710–713)). To date, no neuropathological features or behavioral deficits associated with AD have been described in these animals. However, selective elevations in brain levels of Aβ42 have been found in animals expressing mutant, but not wild-type, PS-1. Gene-targeted PS-1 null mice lacking one or both functional alleles of the PS-1 gene have also been described (Wong et al., Nature 387: 288–292 (1997)). Mice in which both PS-1 alleles have been disrupted resulting in the complete loss of PS-1 expression are not viable and die shortly after birth. No abnormal phenotypes or changes in APP processing have been reported in mice lacking only one of the two PS-1 alleles.

SUMMARY OF THE INVENTION

This invention discloses a gene-targeted, non-human mammal and generational offspring comprising the gene encoding the mutant protein product of a mutated FAD gene, more preferably a presenilin 1 FAD gene (PS-1), and still more preferably a gene-targeted mouse comprising the gene sequence encoding the mutant protein product of PS-1 which has been mutated to contain the human P264L mutation (Wasco et al., Nature Medicine 1: 848, (1995)). In particular, this invention discloses a mouse wherein a part of a mouse presenilin 1 gene encoding presenilin 1 protein has been replaced with a DNA sequence that results in a mouse presenilin 1 gene that contains the human P264L mutation. In humans, the P264L mutation causes an increased amount of amyloid protein Aβ42 as well as clinical manifestations of AD. Still more specifically, the base sequence of codon 264 of the mouse presenilin 1 gene is altered from CCG to CTT, which is the base sequence found to constitute the P264L mutation of humans. The mutated gene codon encodes leucine in place of proline in amino acid number 264 of presenilin 1. Additionally, and still more specifically, a nucleotide base in codon 265 of the mouse presenilin 1 gene is altered from adenosine to guanosine, but this change does not result in an amino acid change in the expressed protein. However, the combined sequence of codons 264 and 265, after the incorporation of the most preferred changes described above, results in a restriction enzyme site for the restriction enzyme AflIII.

Accordingly, in one embodiment, this invention features a non-human mammal and generational offspring homozygous for a targeted mutant PS-1 gene comprising a mutated FAD gene preferably a mouse presenilin 1 protein-encoding sequence comprising a human P264L mutation in place of the native presenilin 1 protein-encoding sequence. In another embodiment, the invention features a non-human mammal and generational offspring heterozygous for a targeted PS-1 gene comprising a mutated mouse FAD gene, preferably a mouse presenilin 1 protein-encoding sequence containing a human P264L mutation in place of the native presenilin 1 protein-encoding sequence.

DETAILED DESCRIPTION

Figure 1:
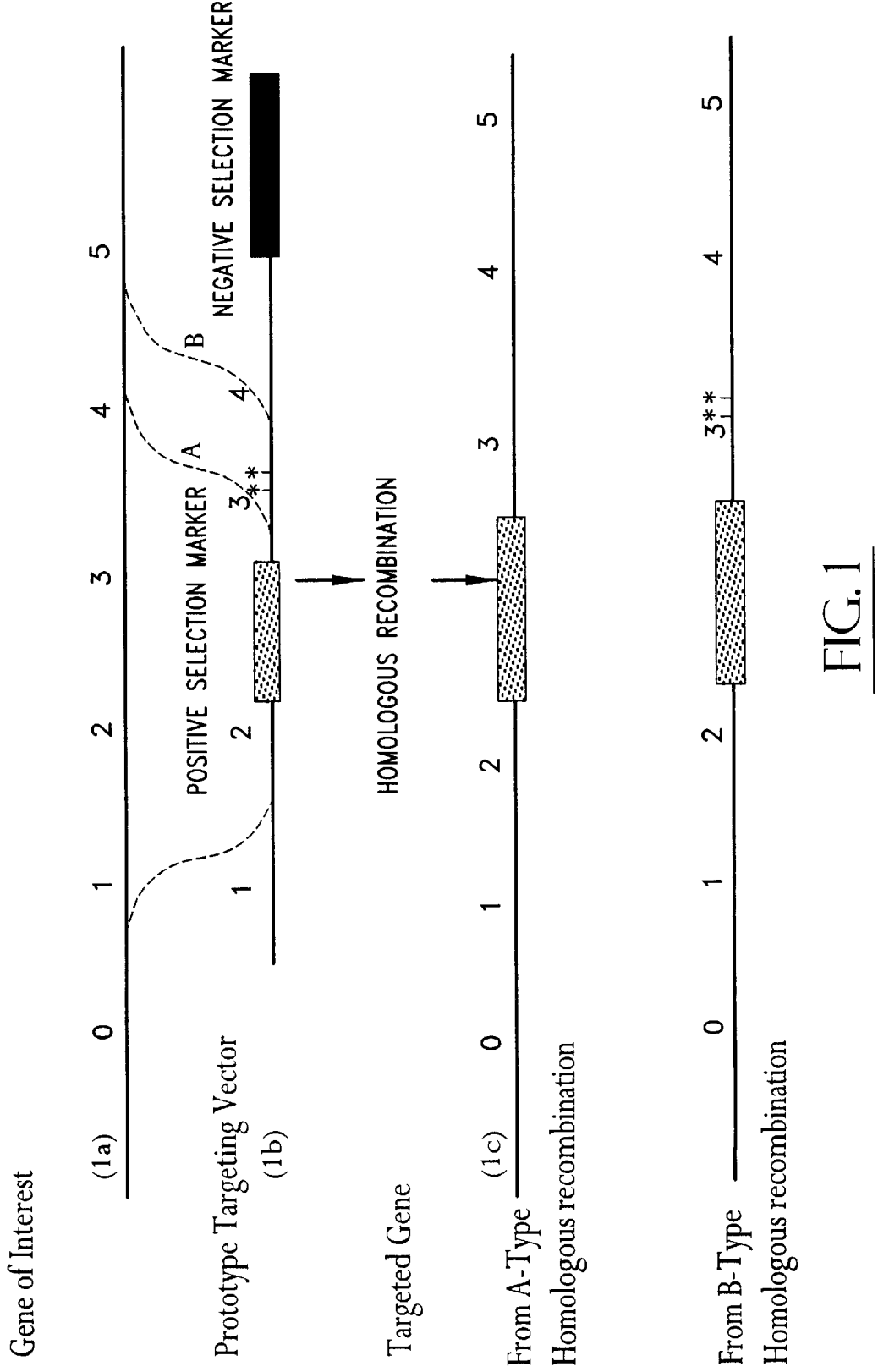
FIG. 1 is a schematic diagram illustrating general principles of gene targeting showing a representative gene of interest (1a), a representative prototype targeting vector (1b), and a representative targeted gene (1C).

This invention provides a gene-targeted, non-human mammal (and generational offspring of such mammal) that contains in the non-human mammal's endogenous (i.e., native) presenilin 1 gene the human P264L mutation. Most preferably, the gene-targeted, non-human mammal produces a mutated presenilin 1 protein instead of the presenilin 1 protein normally produced by the non-human mammal. Gene-targeted, non-human mammals homozygous for a presenilin 1 gene containing the human P264L mutation produce the mutated presenilin 1 protein exclusively. Gene-targeted, non-human mammals heterozygous for a presenilin 1 gene containing the human P264L mutation produce both the mutated presenilin 1 protein and the native presenilin 1 protein. Preferably, the gene-targeted, non-human mammal of this invention is a rodent, and more specifically a mouse.

Importantly, because the non-human mammal of this invention is generated by gene targeting, as opposed to transgenic techniques, the mammal produces the mutated presenilin 1 protein exclusively by normal endogenous presenilin 1 protein processing mechanisms. Advantageously, and unlike the processing resulting from transgenic approaches, the presenilin 1 protein undergoing such processing is expressed from genes having the normal copy number, and under the control of the endogenous presenilin 1 gene expression control mechanisms. As a result, the presenilin 1 protein in the non-human animal of this invention is produced with the same development timing, same tissue specificity, and same rates of synthesis normally associated with native presenilin 1 protein in the gene-targeted, non-human mammal.

The gene-targeted, non-human mammals of this invention may be used as tools or models to elucidate the role of PS-1 comprising the human P264L mutation in the pathology and symptomatology of AD. They may be used to elucidate the manner in which the P264 mutation increases the production of the amyloid protein Aβ42. As used herein, the term "increase" when used in the forgoing context, means that the levels of Aβ42 produced by the non-human mammals disclosed herein are elevated relative to wild-type controls.

The non-human mammals of this invention and generational offspring also may be used as assay systems to screen for in vivo inhibitors and for discovering and testing the efficacy and suitability of putative chemicals compounds for their ability to inhibit the formation, presence and deposition of excessive amounts of Aβ42 in the brain tissues, other tissues and body fluids (e.g., blood and cerebral spinal fluid), said method comprising the steps of: (a) administering said chemical compounds to a non-human mammal homozygous or heterozygous for a targeted mutant PS-1 gene comprising the human P264L mutation comprising: a mouse PS-1 peptide-encoding sequence containing a human P264L mutation in place of the native PS-1 peptide-encoding sequence and (b) measuring the relative amounts of Aβ42 in brain tissues, other tissues and body fluids (or some combination thereof) of said non-human mammal, at an appropriate interval of time after the administration of said chemical compounds.

As used in this disclosure, the following terms and phrases have the following indicated definitions.

As used herein, "arms of homology" means nucleotide DNA sequences in a targeting vector: (1) which have sufficient length and homology to provide for site-specific integration of part of the targeting vector into the target gene by homologous recombination; (2) in which, or between which are located one or more mutations to be introduced into a target gene; and (3) which flank a positive selectable marker.

As used herein, "homologous recombination" means rearrangement of DNA segments, at a sequence-specific site (or sites), within or between DNA molecules, through base-pairing mechanisms.

As used herein, "human P264L mutation" means the following: the nucleotide sequence of codon 264 of the presenilin 1 gene is changed from CCG to a sequence selected from the group consisting of: CTT; CTC; CTA; CTG; TTA; TTG; and most preferably changed from CCG to CTT. Additionally, the nucleotide sequence of codon 265 of the presenilin 1 gene optionally, but preferably, is changed from AAA to AAG. The above described most preferable change of base sequences in codon 264 constitute the human P264L mutation. The optional, but preferred, change of the base sequence of codon 265 adds an AflII cleavage site to the gene.

As used herein, "target gene" or "targeted gene" means a gene in a cell, which gene is to be modified by homologous recombination with a targeting vector.

As used herein, "gene targeted, non-human mammal" means a non-human mammal comprising one or more targeted genes via a gene-targeting, as opposed to transgenic, approach.

As used herein, "generational offspring" in relationship to "gene targeted, non-human mammal" means an animal whose genome includes the same gene targeted manipulation as the parent(s) of that offspring. For example, and not limitation, where a mammal whose genome has been manipulated by gene targeting techniques to include a human mutation is then used for breeding purposes, all subsequent generations derived from that first mammal(s) are considered "generational offspring" so long as the genome(s) of such subsequent generational offspring comprises the gene-targeted manipulation as the original mammal; by design, this definition does not exclude other genomic-manipulations which may also be present in such generational offspring, nor does this definition require that such generational offspring be derived solely by cross-breeding techniques between a male and female mammal.

As used herein, "transgenic non-human mammal" means a non-human mammal in which a foreign ("transgene") gene sequence has been inserted randomly in a non-human mammal's genome and is therefore expressed in addition to all normally-expressed native genes (unless the inserted transgene has interrupted a gene thus preventing its expression).

As used herein, "targeting vector" or "replacement vector" means a DNA molecule that includes arms of homology, the nucleotide sequence (located within or between the arms of homology) to be incorporated into the target gene, and one or more selectable markers.

As used herein, "wild type control animal" means a non-gene targeted, non-human mammal of the same species as, and otherwise comparable to (e.g., similar age), a gene-targeted non-human mammal as disclosed herein. A wild-type control animal can be used as the basis for comparison, in assessing results associated with a particular genotype.

Other features and advantages of the invention will be apparent from the following description of the preferred embodiments thereof, and from the claims.

The first step in producing a gene-targeted non-human mammal of this invention is to prepare a DNA targeting vector. The targeting vector is designed to replace, via homologous recombination, part of the endogenous presenilin 1 gene sequence of a non-human mammal, so as to introduce the P264L human mutation. The targeting vector is used to transfect non-human mammalian cell, e.g., a pluripotent, murine embryo-derived stem ("ES") cell. In this cell, homologous recombination (i.e., the gene-targeting event) takes place between the targeting vector and the target gene. The mutant cell is then used to produce intact non-human mammals (e.g., by aggregation of murine ES cells to mouse embryos) to generate germ-line chimeras. The germline chimeras are used to produce siblings heterozygous for the mutated targeted gene. Finally, interbreeding of heterozygous siblings yields non-human mammals (e.g., mice) homozygous for the mutated target gene.

Targeting vectors for the practice of this invention can be constructed using materials, information and processes known in the art. A general description of the targeting vector used in this invention follows.

A targeting vector or replacement vector for use in this invention has two essential functions: (1) to integrate specifically (and stably) at the endogenous presenilin 1 target gene; and (2) to replace a portion of exon 8 of the endogenous presenilin 1 gene, thereby introducing the P264L human mutation and the mutation that introduces a new cleavage site in the gene. Those two essential functions depend on two basic structural features of the targeting vector.

The first basic structural feature of the targeting vector is a pair of regions, known as "arms of homology", which are homologous to selected regions of the endogenous presenilin 1 gene or regions flanking the presenilin 1 gene. This homology causes at least part of the targeting vector to integrate into the chromosome, replacing part (or all) of the presenilin 1 target gene, by homologous recombination.

Homologous recombination, in general, is the rearrangement of DNA segments, at a sequence-specific site (or sites), within or between DNA molecules, through base-paring mechanisms. The present invention relates to a particular form of homologous recombination sometimes known as "gene targeting".

The second basic structural feature of the targeting vector consists of the actual base changes (mutation(s)) to be introduced into the target gene. In the present invention, the base changes in codon 264 of exon 8 resulted in an amino acid change in amino acid 264 from proline to leucine when the mutated gene was expressed to make protein.

The mutation(s) to be introduced into the presenilin I target gene must be located within the "arms of homology".

Gene targeting, which affects the structure of a specific gene already in a cell, is to be distinguished from other forms of stable transformation, wherein integration of exogenous DNA for expression in a transformed cell is not site-specific, and thus does not predictably affect the structure of any particular gene already in the transformed cell. Furthermore, with the type of targeting vector preferred in the practice of this invention (e.g., the one disclosed below), a reciprocal exchange of genomic DNA takes place (between the "arms of homology" and the target gene), and chromosomal insertion of the entire vector is advantageously avoided.

The examples of this patent disclosure set forth the construction of a presenilin 1 gene targeting vector (and its use) to mutate the murine presenilin 1 protein encoding sequence so that it encodes the murine presenilin 1 protein, containing the human P264L mutation and an additional cleavage site. One of ordinary skill in the art will recognize that numerous other targeting vectors can be designed to introduce the same mutations, using the principles of homologous recombination. Gene-targeted, non-human mammals produced using such other targeting vectors are within the scope of the present invention. A discussion of targeting vector considerations follows.

The length of the arms of homology that flank the replacement sequence can vary considerably without significant effect on the practice of the invention. The arms of homology must be of sufficient length four effective heteroduplex formation between one strand of the targeting vector and one strand of a transfected cell's chromosome, at the presenilin 1 target gene locus. Increasing the length of the arms of homology promotes heteroduplex formation and thus targeting efficiency. However, it will be appreciated that the incremental targeting efficiency accruing per additional homologous base pair eventually diminishes and is offset by practical difficulties in target vector construction, as arms of homology exceed several thousand base pairs. A preferred length for each arm of homology is 50 to 10,000 base pairs.

There is considerable latitude in the choice of which regions of the presenilin 1 target gene, i.e., chromosomal regions flanking the presenilin 1 target gene, are represented in the targeting vector's arms of homology. The basic constraint is that the base pairs to be changed in the presenilin 1 target gene must lie within the sequence that constitutes the arms of homology. The arms of homology may lie within the presenilin 1 target gene, but it is not necessary that they do so and they may flank the presenilin 1 target gene.

Preferably, the targeting vector will comprise, between the arms of homology, a positive selection marker. The positive selection marker should be placed within an intron of the target gene, so that it will be spliced out of mRNA and avoid the expression of a target/marker fusion protein. More preferably the targeting vector will comprise two selection markers; a positive selection marker, located between the arms of homology, and a negative selection marker, located outside the arms of homology. The negative selection marker is a means of identifying and eliminating clones in which the targeting vector has been integrated into the genome by random insertion instead of by homologous recombination. Exemplary positive selection markers are neomycin phosphotransferase and hygromycin β phosphotransferase genes. Exemplary negative selection markers are Herpes simplex thymidine kinase and diphtheria toxin genes.

To eliminate potential interference on expression of the target protein, the positive selection marker can be flanked by short loxP recombination sites isolated from bacteriophage P1 DNA. Recombination between the two loxP sites at the targeted gene locus can be induced by introduction of cre recombinase to the cells. This results in the elimination of the positive selection marker, leaving only one of the two short loxP sites. (see U.S. Pat. No. 4,959,317, which is herein incorporated by reference). Excision of the positive selectable marker from intron 8 of the mutated presenilin 1 gene can thus be effected.

FIG. 1 illustrates the general principles of gene-targeting for introducing mutations into a mammalian genome using homologous recombination (reviewed in Capecchi, M. R,. *Trends Genet* 5: 70–76 (1989); Koller and Smithies, Ann. Rec. *Immunol.* 10: 705–730 (1992)). A length of genomic DNA is first depicted by organizing it into regions (numbered 0–5 in FIG. 1a). In FIG. 1, several base pair changes (from 1–10) are to be incorporated into the cellular DNA around region 3. Homologous recombination using a gene targeting vector is utilized. The type of gene targeting vector used to incorporated these changes is termed a replacement vector.

As defined previously, a "replacement vector" herein refers to a vector that includes one or more selectable marker sequences and two contiguous sequences of ES cell genomic DNA that flank a selectable marker. These flanking sequences are termed "arms of homology". In FIG. 1b, the arms of homology are represented by regions 1–2 and 3–4. The use of DNA derived from the ES cells (isogenic DNA) helps assure high efficiency recombination with the target sequences (te Riele et al., Proc. Natl. Acad Sci. USA 89: 5128–5132 (1992)). The arms of homology are placed in the vector on either side of a DNA sequence encoding resistance to a drug toxic to the ES cells (positive selection marker). A gene encoding susceptibility to an otherwise nontoxic drug (negative selection marker) is placed outside the region of homology. In the replacement vector used in this invention, the positive selection marker is neo$^r$, a gene that encodes resistance to the neomycin analog G418, and the negative selection marker is the herpes simplex virus thymidine kinase gene (HSV-tk) that encodes susceptibility to gancyclovir. When this replacement vector is introduced into ES cells via transfection and its DNA undergoes homologous recombination with ES cellular DNA, the positive selection marker is inserted into the genome between regions 2 and 3 in this example (making the transformed cells resistant to G418) while the negative selection markers is excluded (making the cells resistant to gancyclovir). Thus, to enrich for homologous recombinants, transfected ES cells are grown in culture medium containing G418 to select for the presence of the neo$^r$ gene and gancyclovir to select for the absence of the HSV-TK gene.

If base pair changes (mutations) are introduced into one of the arms of homology it is possible for these changes to be incorporated into the cellular gene as a result of homologous recombination. Whether or not the mutations are incorporated into cellular DNA as a result of homologous recombination depends on where the crossover event takes place in the arm of homology bearing the changes. For example, as depicted by scenario "A" in FIG. 1, the crossover in the arm occurs proximal to the mutations and so they are not incorporated into cellular DNA. In scenario "B", the crossover takes place distal to the position of the mutations and they are incorporated into cellular DNA. Because the location of the crossover event is random, the frequency of homologous recombination events that include the mutations is increased if they are placed closer to the positive selection marker.

By the above method, the skilled artisan can achieve the incorporation of the selectable marker at a preselected location in the gene of interest flanked by specific base pair changes. Presumably, the artisan would preferably choose to have the selectable marker incorporated within the intron of the gene of interest so as not to interfere with endogenous gene expression while the mutations would be included in adjacent coding sequence so as to have make desired changes in the protein product of interest (FIG. 1), (Askew, et al., Mol Cell Biol 13: 4115–4124 (1993), Fiering, et al., Proc. Natl. Acad. Sci. USA 90: 8469–8473 (1993); Rubinstein, et al., Nuc. Acid Res. 21: 2613–2617 (1993), Gu, et al., Cell 73: 1155–1164 (1993), Gu, et al., Science 265: 103–106 (1994))

In order that the invention disclosed herein may be more efficiently understood, examples are provided below. It should be understood that these examples are for illustrative purposes only and are not to be construed as limiting to the invention in any manner. Throughout these examples, molecular cloning reactions, and other standard recombinant DNA techniques, were carried out according to methods described in Maniatis et al, Molecular Cloning—A Laboratory Manual, 2$^{nd}$ ed, Cold Spring Harbor Press (1989) (hereinafter, "Maniatis et al."), using commercially available enzymes, except where otherwise noted.

EXAMPLES

Example 1

Cloning of Mouse PS-1 Exon 8 Region

Figure 2:
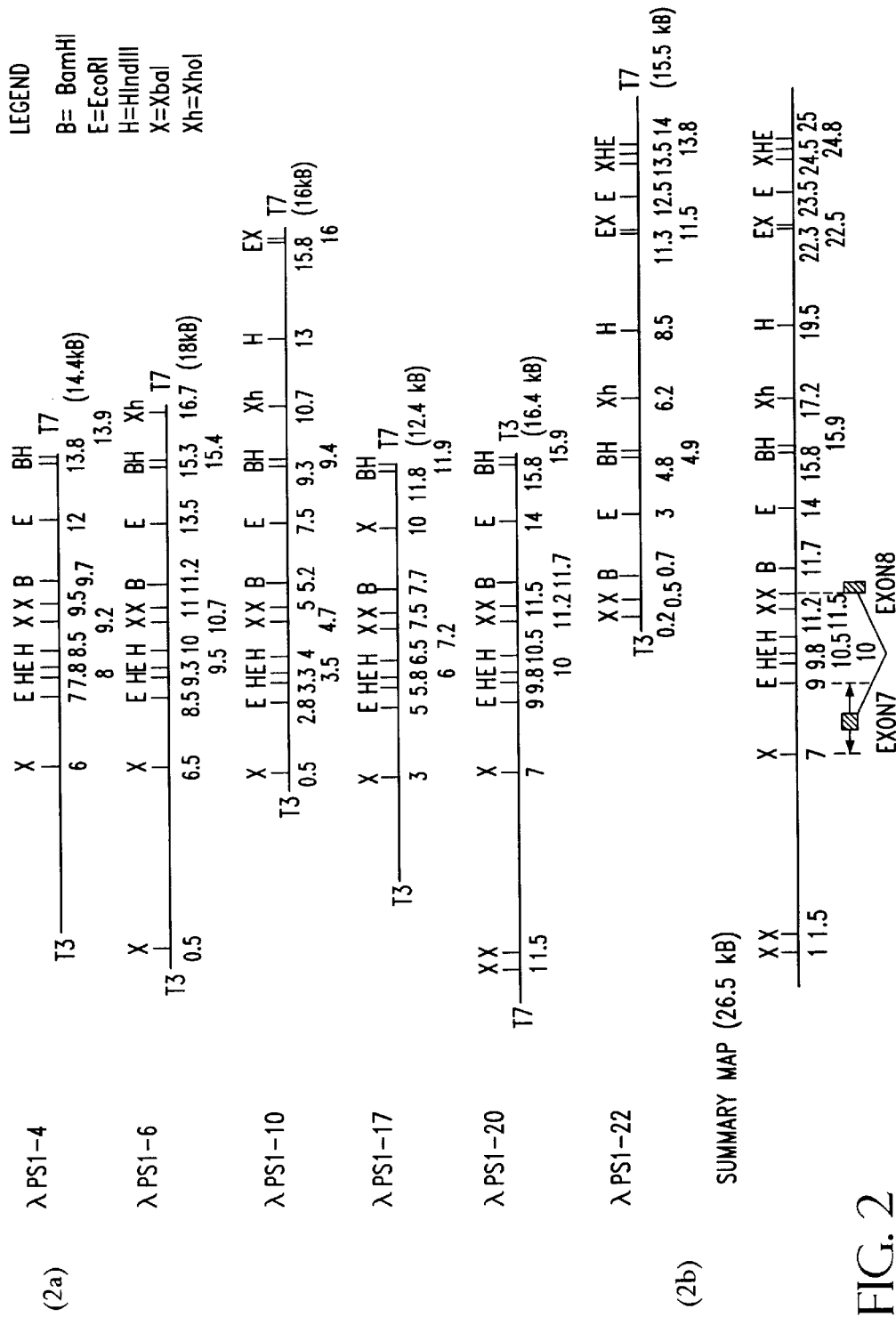
FIG. 2 is a set of mouse PS-1 genomic clone maps prepared using the Flash™ Non-radioactive Gene Mapping Kit. Letter abbreviations for restriction endonucleases are as follows: E, EcoRI; X, XbaI; H, HindIII; B, BamHI; Xh, XhoI.

The mouse PS-1 genomic DNA was cloned from a bacteriophage library created from 129/Sv mouse DNA partially digested with Sau3A and into the BamHI site of Lambda DASH™ II (Reaume, et al., Science 267: 1831–1833, (1995)). Using standard molecular biology techniques (Maniatis, et al.), approximately $1.2 \times 10^6$ recombinant bacteriophages were screened for the presence of PS-1 sequences by hybridization with a small, radiolabelled PS-1-specific DNA probe. This 477 base pair PS-1 probe was generated by polymerase chain reaction (PCR) amplification (Mullis et al., Methods Enzymol. 155: 335–350, (1987)) of mouse genomic DNA using primers R892 (CTC ATC TTG GCT GTG ATT TCA; SEQ ID NO. 1) and R885 (GTT GTG TTC CAG TCT CCA; SEQ ID NO. 2) which hybridize to the 3' end of exon 7 and the 5' end of exon 11 respectively (FIG. 2). The amplified fragment was separated from other components of the reaction by electrophoresis on a 1.0% agarose gel, and purified using GeneClean®II (Bio 101, Inc., La Jolla, Calif.). Purified probe DNA was radioactively labelled with $^{32}$P-dCTP by the random primer method using materials and methods supplied by the kit manufacturer (Multiprime DNA Labeling System; Amersham Life Sciences, Arlington Heights, Ill.).

From this screen, 13 clones were identified that hybridized to the PS-1 probe. The clones were identified as: λPS1-4, λPS1-5, λPS1-6, λPS1-10, λPS1-11, λPS1-17, λPS1-19, λPS1-20, λPS1-22, λPS1-24, λPS1-28; λPS1-31, and λPS1-35. These clones were purified by limiting dilution and plaque hybridization with the PS-1 probe (Maniatis, et al.).

Figure 3:
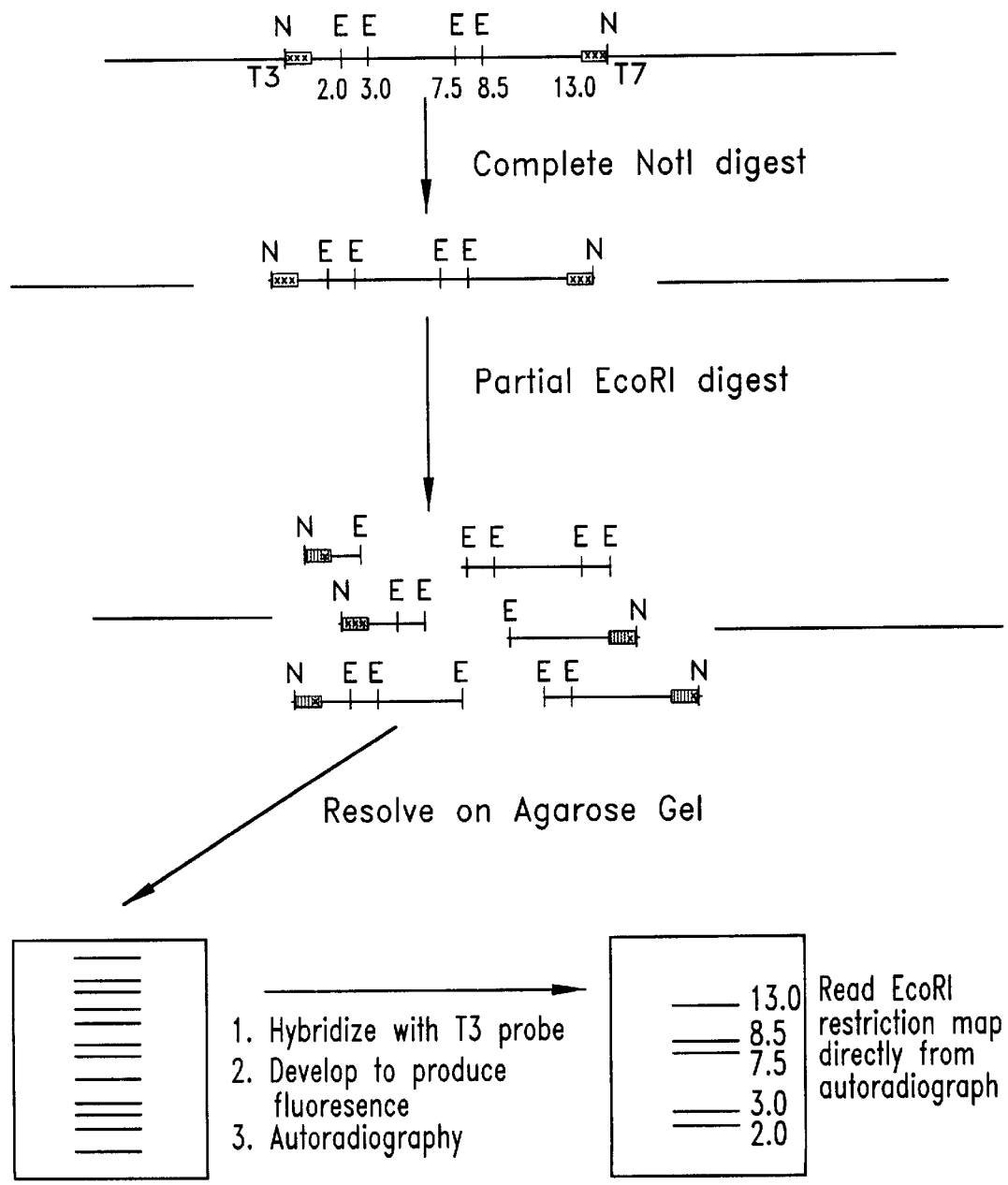
FIG. 3 is a representative restriction map used to illustrate a Flash™ restriction mapping method.

From each clone, DNA was prepared from bacteriophage particles purified on a CsCl gradient (Maniatis, et al.). Restriction maps were then generated for each of the cloned inserts using the FLASH™ Non-radioactive Gene Mapping Kit (Stratagene® Inc., La Jolla, Calif.). A typical restriction map generated by this method is illustrated in FIG. 3. This method of restriction enzyme mapping involves first completely digesting 10 μg of the bacteriophage DNA with the restriction enzyme NotI using standard restriction enzyme digest conditions (Maniatis, et al.). NotI cuts all clones in the vector DNA at either end of the cloned insert so as to leave a T3 bacteriophage promoter attached to one end of the insert and a T7 bacteriophage promoter attached to the other end. The NotI digested DNA is then partially digested with the enzyme EcoRI, as an example, using limiting amounts of enzyme (0.2 units/μg DNA) in an 84 μl reaction volume at 37° C. Aliquots (26 μl) were removed after 3 minutes, 12 minutes and 40 minutes and the digest reaction was stopped by the addition of 1μl of 0.5 M EDTA. DNA from all three time points was resolved on a 0.7% agarose gel, visualized by ethidium bromide staining, and then transferred to a GeneScreen Plus® membrane (NEN® Research Products, Boston, Mass.) by capillary transfer (Maniatis, et al., supra). The membrane was hybridized with an alkaline phosphatase labelled oligonucleotide that was specific for the T3 promoter (supplied with the FLASH™ kit) using reagents and methods supplied by the kit manufacturer. After hybridization, the membrane was washed and developed with a chemiluminescent-yielding substrate and then exposed to X-ray film in the dark for approximately 60 minutes.

The oligonucleotide probes effectively label one end of the insert. By determining the positions of the bands on the X-ray film and calculating the DNA size to which they corresponded, it was possible to determine the position of the EcoRI sites relative to the T3 end of the insert (FIG. 3). These results could then be complemented by stripping the probe off of the membrane, and rehybridizing with a T7-specific oligonucleotide in order to determine the positions of the EcoRI sites relative to the T7 end of the insert. This process was repeated using the enzymes HindIII and XbaI. By comparing the restriction enzyme maps of the different overlapping clones a composite map was assembled. Of the 13 original clones isolated, 6 independent clones were identified (FIG. 2).

Figure 4:
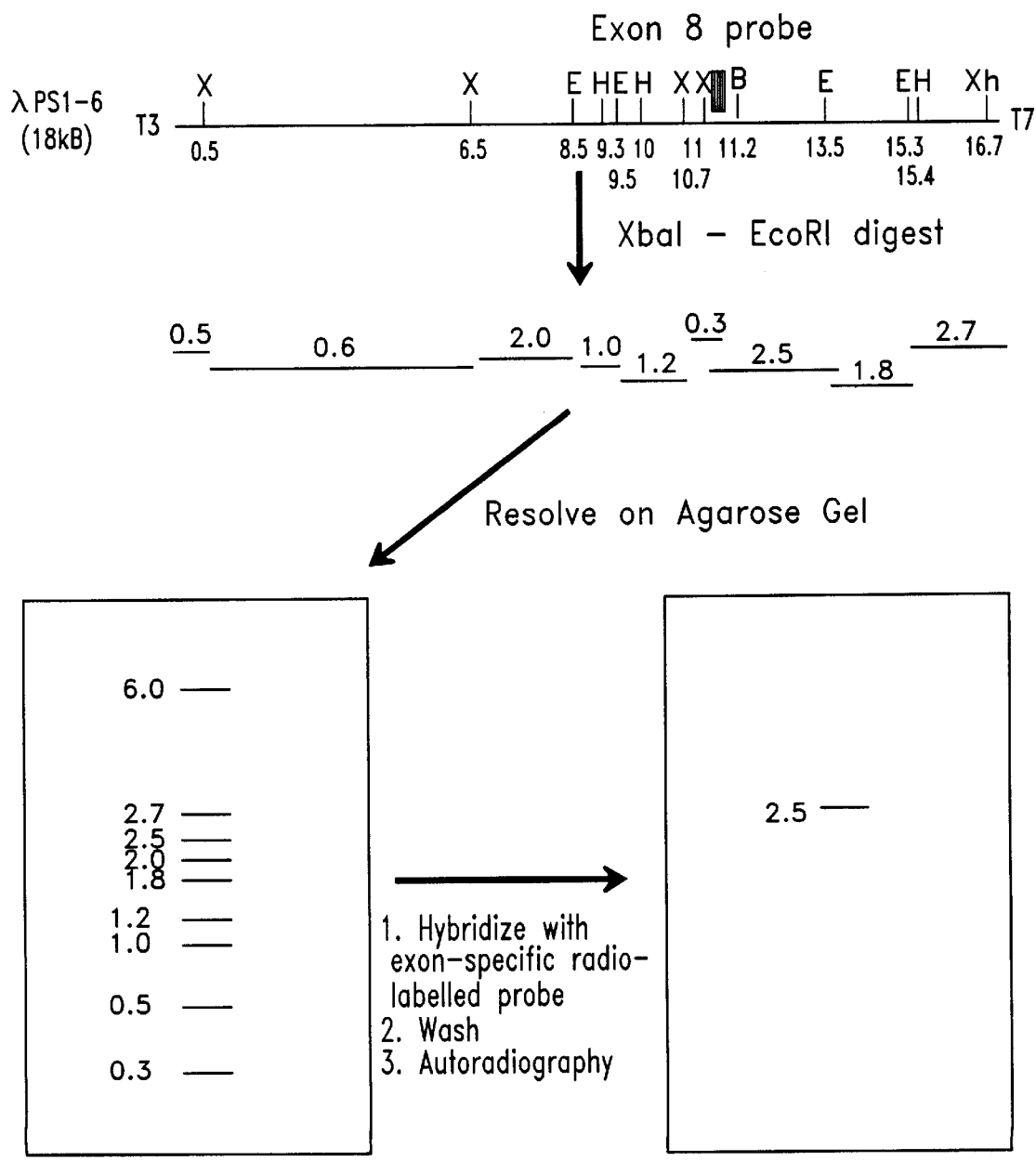
FIG. 4 is a diagram illustrating the strategy for placing exons 7 and 8 on the restriction map of PS-1.

Exon 8 was located on the restriction map hybridizing exon-specific probes to complete digests of each of the 6 different lamda genomic clones. Initially, 3μg of DNA from each of the 6 different clones was completely digested with the restriction enzymes EcoRI and XbaI. The digested DNA was resolved on a 0.8% agarose gel, visualized by means of ethidium bromide staining and transferred to a GeneScreen Plus® membrane by capillary transfer. The membrane was then hybridized with a DNA probe that specifically hybridized to sequences from mouse PS-1 exon 8. This probe was generated by PCR using oligonucleotides FEX8 (ATT TAG TGG CTG TTT TGT G; SEQ ID NO. 3) and REX8 (AGG AGT AAA TGA GAG CTG GA; SEQ ID NO. 4) which hybridize to the 5' and 3' ends of exon 8, respectively. After hybridization, the membrane was washed and exposed to X-ray film (FIG. 4). This experiment revealed that all clones contained a 2.5 kb fragment that hybridized to the exon 8 probe. By combining this information with the restriction map data for each lambda clone, exon 8 was identified on the map (position 11.5 to 14 on the summary map, FIG. 2)

A similar procedure was used to identify the position of exon 7 on our composite map using exon 7-specific probe and utilizing the restriction enzymes XbaI and EcoRI. The exon 7-specific probe was generated using PCR primers F892 (TGA AAT CAC AGC CAA GAT GAG; SEQ ID NO. 5) and PS1-1 (GCA CTC CTG ATC TGG AAT TTT G; SEQ ID NO. 6). Exon 7 was localized to the 2 kb XbaI EcroI fragment of all clones except λPS1-22 which allowed for the determination that exon 7 is located between positions 7.0 and 9.0 on the summary map (FIG. 2).

Exon specific probes were also used to obtain additional restriction map information using additional restriction enzymes. For example, when λPS1-22 was digested with NotI and BamHI, resolved on an agarose gel, transferred to a Genescreen Plus® membrane and probed with the exon 8-specific probe, a 700 bp fragment was identified. This information, when combined with the information from the other bacteriophage clones, allowed placement of the BamHI at position 11.7 on the composite map (FIG. 2). This process was repeated for the restriction enzyme XhoI.

Example 2

Construction of a Replacement Vector

Figure 5:
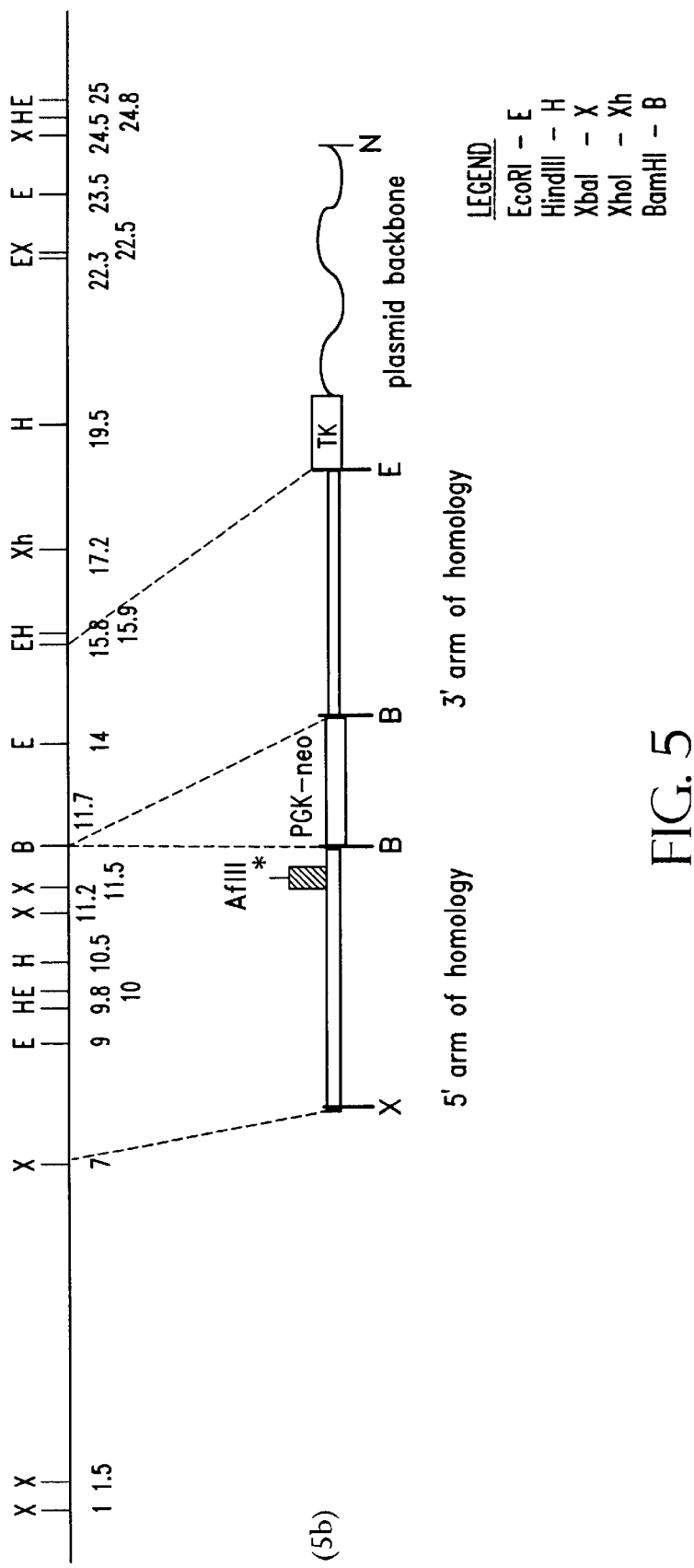
FIG. 5 is a pair of genetic maps illustrating the relationship between Exon 8 of PS-1 and the pPS1-8-TV replacement vector. Letter abbreviations for restriction endonucleases are as follows: E, EcoRI; X, XbaI; H, HindIII; B, BamHI; Xh, XhoI.

A 4.7 kb XbaI-BamHI fragment (which also contains two internal XbaI fragments) located at positions 7.0 to 11.7 on the summary map (FIG. 2), was chosen as the 5' arm that included the necessary mutations and a 4.1 kb BamHI-EcoRI fragment (which also contains an internal EcoRI site) located at positions 11.7 to 15.8 on the summary map (FIG. 2), as a 3' arm. These fragments were isolated first and cloned into pBlueScript® SK+ (Stratagene Cloning Systems, LaJolla, Calif.) and then further subcloned into the plasmid pPNTlox$^2$ (described below) that contained a neo$^r$ gene, an HSV-TK gene and linker sequences to produce a replacement vector (pPS1-8-TV, FIG. 5) with the same general structure as that discussed above.

Figure 6:
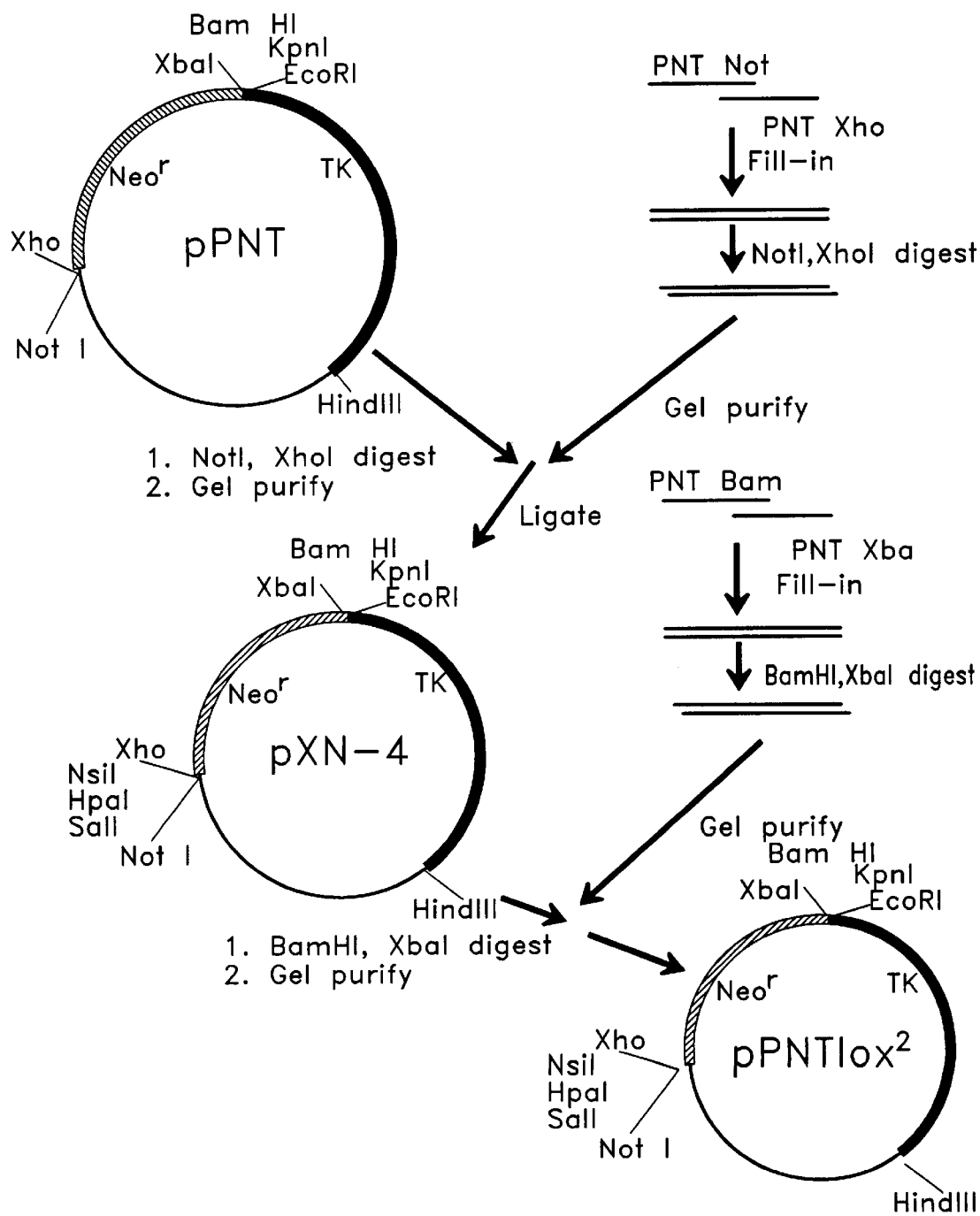
FIG. 6 is a schematic diagram illustrating the construction of plasmid pPNTlox$^2$.

(a) Construction of the Intermediate PlasmidpPNTlox$^2$ pPS1-8-TV was created from pPNT (Tybulewicz, et al., *Cell* 65: 1153–1163 (1991); obtained from Dr. Richard Mulligan, MIT) by first inserting two oligonucleotide linkers on each side of the neo$^r$ cassette creating the intermediate called pPNTlox$^2$ (FIG. 6). A double-stranded 79 base pair 5' linker was created by annealing two single-stranded oligonucleotides that overlap at their 3' ends and then filling in the remaining single-stranded regions with the Klenow fragment of DNA polymerase I. The oligonucleotides PNT Not (GGA AAG AAT GCG GCC GCT GTC GAC GTT AAC ATG CAT ATA ACT TCG TAT; SEQ ID NO. 7) and PNT Xho (GCT CTC GAG ATA ACT TCG TAT AGC ATA CAT TAT ACG AAG TTA TAT GC; SEQ ID NO. 8) (150 ng of each) were combined in a 30 μl reaction mixture containing 5 U of Klenow polymerase, Klenow polymerase buffer and 2 mM dNTPs (dATP, dCTP, dGTP, and dTTP). After incubating for 1 hour at 37° C., a portion (5 μl) of this reaction mixture was simultaneously digested with the restriction enzymes NotI and XhoI to liberate the restriction enzyme sites at each end of the linker. In addition, 200 ng of pPNT was digested with NotI and XhoI. The digested plasmid was resolved on a 0.8% agarose gel, purified from the gel, and treated with calf intestinal phosphatase according to standard methods (Maniatis et al.). A quantity (66 ng) of the double digested linker was ligated to the double digested and phosphatase-treated pPNT DNA (Maniatis et al.). Following DNA transformation of competent WM1100 *E. coli* (Dower, *Nucleic Acids Res.* 16: 6127–6145 (1988)), plasmid DNA was isolated from ampicillin-resistant bacteria (Holmes et al., *Anal. Biochem.* 114: 193–197 (1981)) and analyzed by restriction enzyme analysis. The proper recombinant plasmids were identified as having acquired SalI, HpaI and NsiI sites (present in the linker) while still retaining the NotI and XhoI sites of the starting plasmid. One such recombinant plasmid with a 79 bp linker sequence was identified and called pXN-4 (FIG. 6).

A similar approach was used to insert a 3' linker between the XbaI and BamHI sites of pXN-4. The oligonucleotides used to synthesize the linker were PNT Xba (CGT TCT AGA ATA ACT TCG TAT AAT GTA TGC TAT; SEQ ID NO. 9) and PNT Bam (CGT GGA TCC ATA ACT TCG TAT AGC ATA CAT TAT; SEQ ID NO. 10). In this case, pXN-4 and the double-stranded linker DNA were digested with XbaI and BamHI. The purified fragments were joined by DNA ligation and transformed into competent WM 1100 bacteria. Plasmid DNA was digested with XbaI and BamHI, end-labelled with $^{32}$P-dCTP and Klenow polymerase, and resolved on an 8% acrylamide gel (Maniatis et al., 1982 supra). The gel was dried and exposed to X-ray film. Proper recombinant clones were identified by the presence of a 40 base pair band liberated by the XbaI-BamHI double digest. The resulting plasmid was designated "pPNTlox$^2$" (FIG. 6).

To confirm the sequences of the inserted linkers, a fragment containing both linkers was isolated from pPNTlox$^2$ using NotI and EcoRI and cloned into pBlueScript® SK+, a vector that was more amenable to nucleotide sequencing. Identity of the linkers was confirmed by direct nucleotide sequencing (Sanger, *Proc. Natl. Acad. Sci. USA* 74: 5463–5467 (1977)) using T3 and T7 sequencing primers (Stratagene® Inc., La Jolla, Calif.) and Sequenase Version 2.0 DNA Sequencing Kit (United States Biochemical, Cleveland, Ohio).

Figure 7:
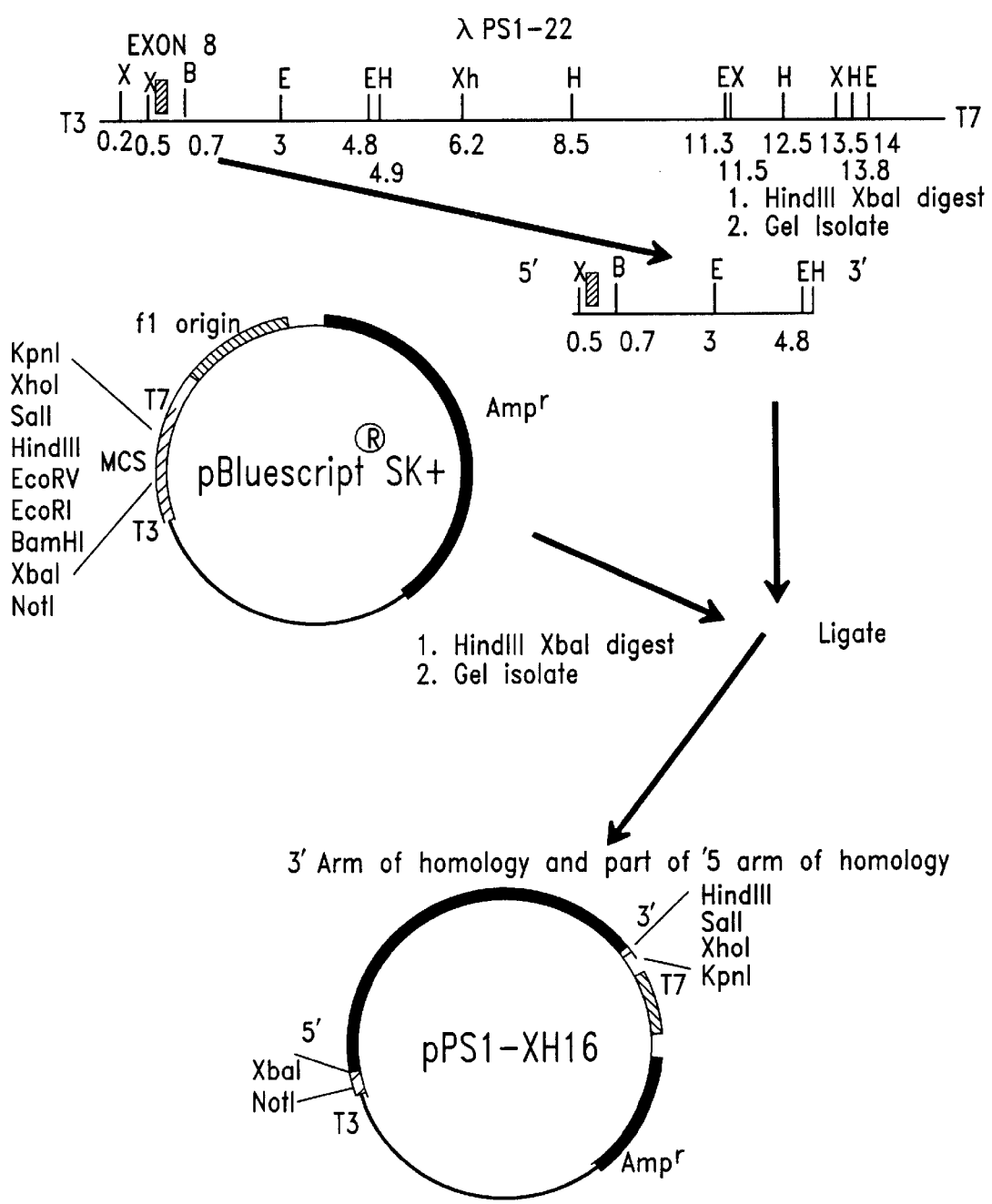
FIG. 7 is a schematic diagram illustrating the construction of plasmid pPS1-XH16.

(b) Subcloning arms of homology. An XbaI-HindIII fragment (positions 11.5 to 15.9 on the summary map, FIG. 2) containing the 3' arm of homology and the fragment used for in vitro mutagenesis was first isolated from λPS1-22 by digesting 30 μg of the phage DNA with XbaI and HindIII, resolving the digested DNA on a 0.8 agarose gel, visualizing the DNA with ethidium bromide staining and then excising the 4.4 kb fragment from the gel. DNA was purified from the gel using GeneClean® II (Bio101 Inc., La Jolla, Calif.). Simultaneously, 1 μg of pBlueScript® SK+ was digested with XbaI and HindIII and subsequently purified by the same procedure. Approximately 400 ng of the purified lambda DNA and 100 ng of the purified plasmid DNA were combined in a 10 μl ligation reaction. Following transformation of competent WM100 *E. coli*, plasmid DNA was isolated from ampicillin-resistant bacteria and analyzed by restriction enzyme analysis to identify the resultant plasmids (FIG. 7). In this case, plasmid DNA from transformed bacteria was first analyzed by digesting it with XbaI and HindIII in order to determine whether the plasmid DNA had acquired the 4.4 kb PS-1 fragment. This plasmid was designated "pPS1-XH16".

Figure 8:
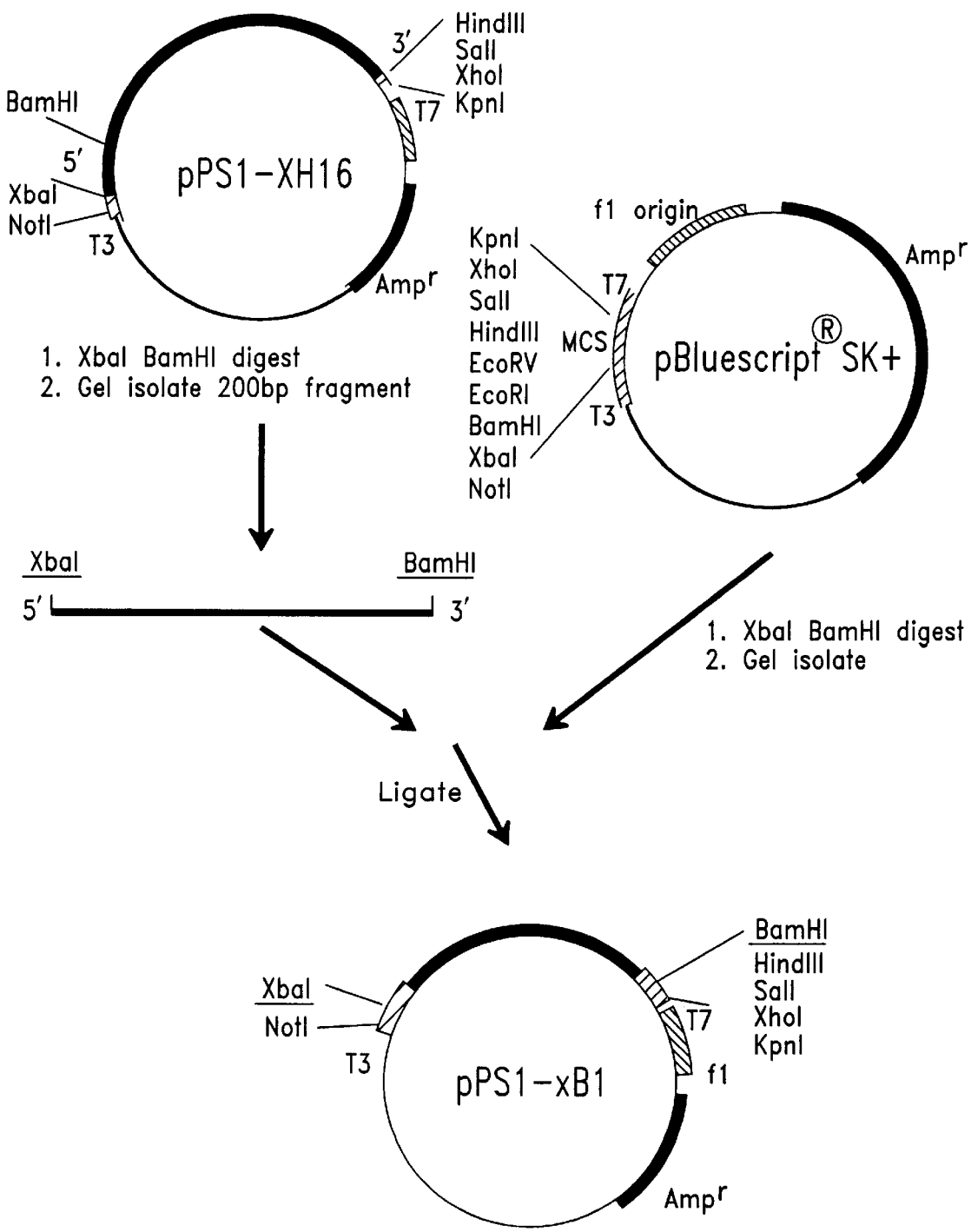
FIG. 8 is a schematic diagram illustrating the construction of plasmid pPS1-XB1.

Similar procedures were used to isolate a 200 bp XbaI-BamHI fragment from pPS1-XH16 and subclone it into pBlueScript® SK+. The resulting plasmid was designated "pPS1-XB1" (FIG. 8).

Figure 9:
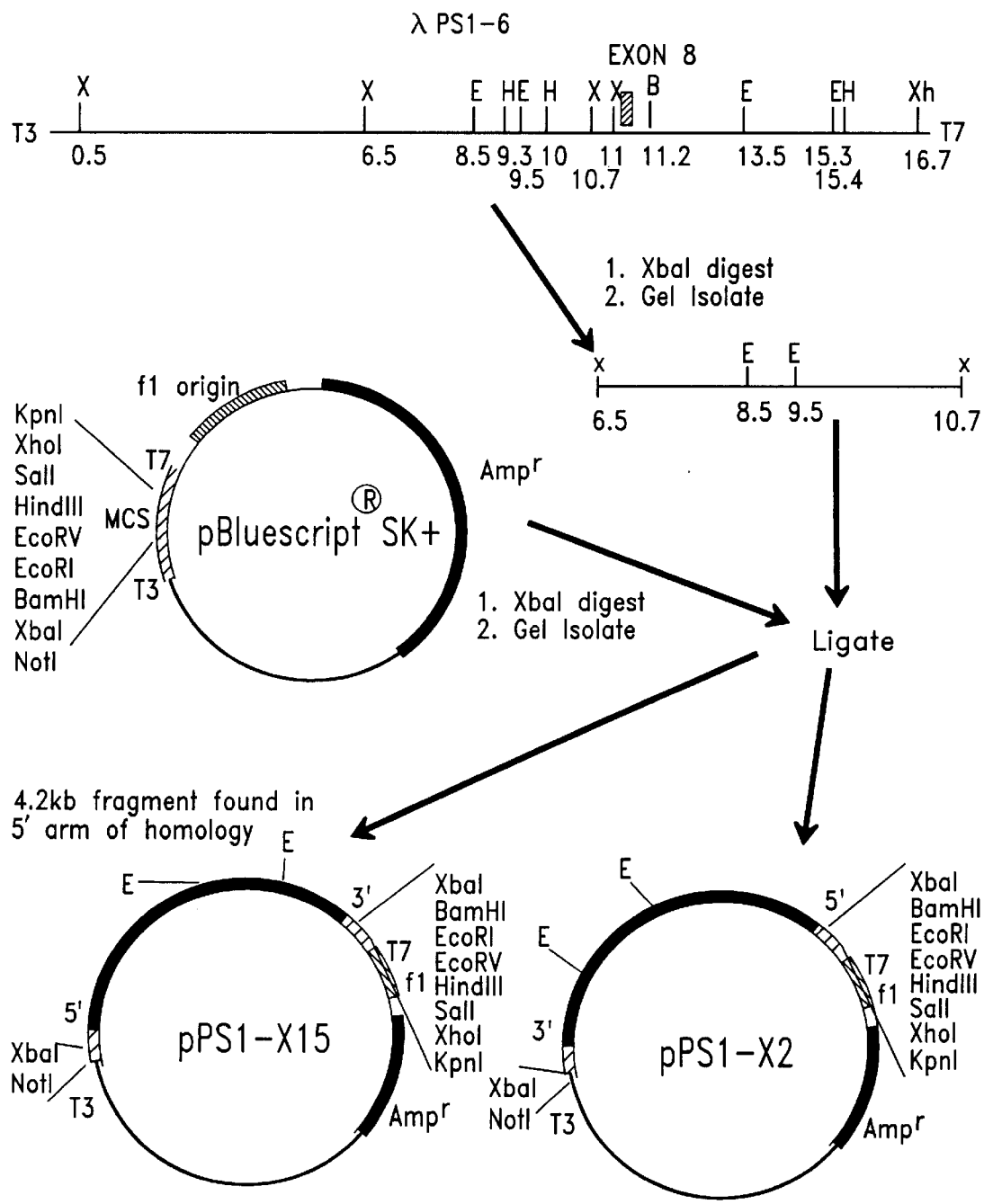
FIG. 9 is a schematic diagram illustrating the construction of plasmids pPS1-X15 and pPS1-X2.

One of the fragments in the 5' arm of homology (a 4.2 kb XbaI fragment (positions 7.0 to 11.2 on summary map; FIG. 2) was similarly subcloned from λPS1-6 into pBlueScript® SK+ and designated "pPS1-X15" (FIG. 9). Because this insert could be positioned in the plasmid in either of two orientations, plasmid DNA was further screened by digesting it with the enzyme EcoRI. In this way, it was determined that the clone pPS1-X15 had the PS-1 insert oriented such that the 5' end was closest to the T3 promoter while in pPS1-X2 the 5' end was adjacent to the T7 promoter (FIG. 9).

Figure 10:
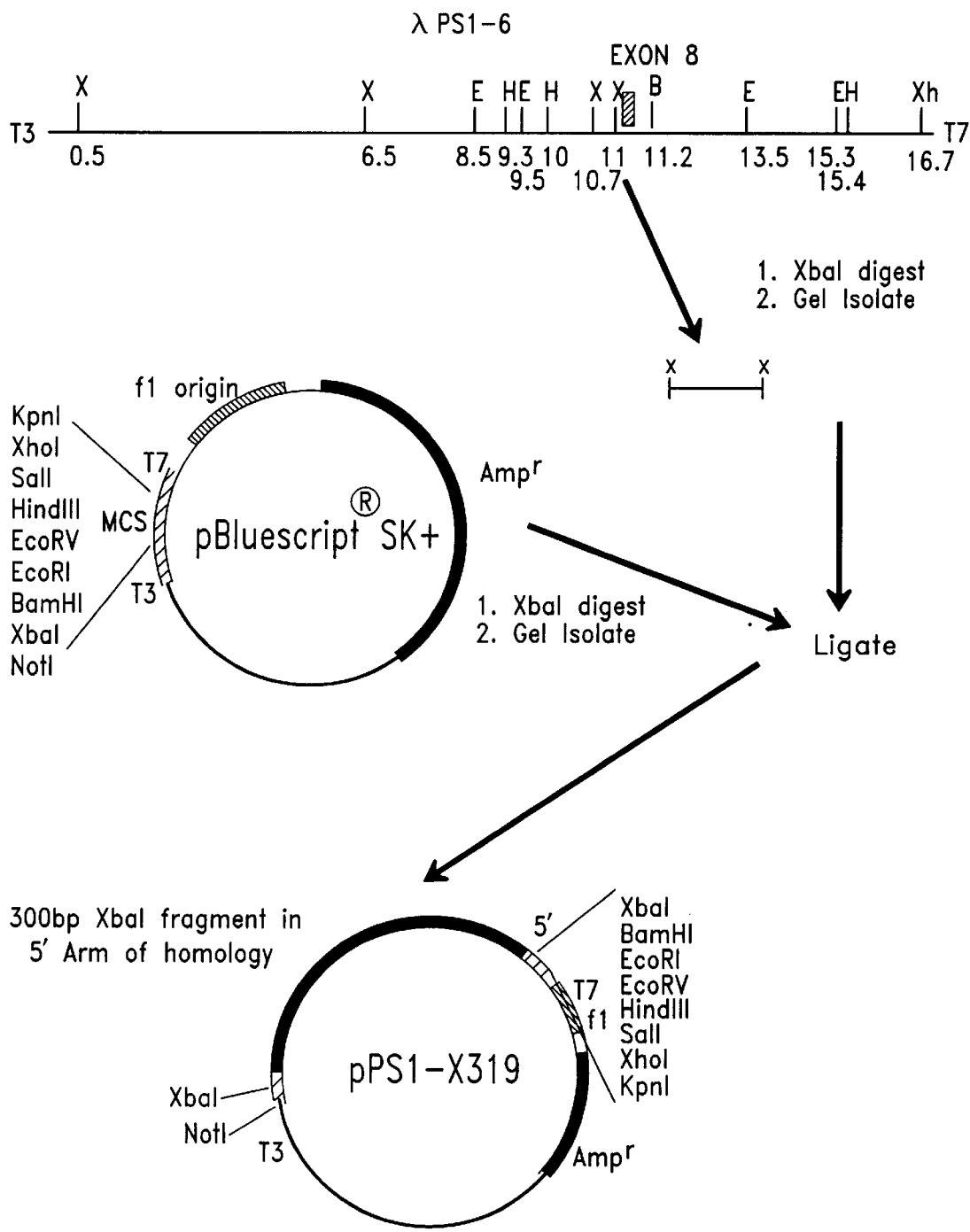
FIG. 10 is a schematic diagram illustrating the construction of plasmid pPS1-X319.

The 300 bp XbaI fragment in the 5' arm (position 11.2 to 11.5 on summary map; FIG. 2) was also similarly cloned into pBlueScript® SK+ from λPS1-20 and named pPS1-X319 (FIG. 10). In this case, the orientation of the XbaI fragment was not determined by subsequent restriction mapping.

Figure 11:
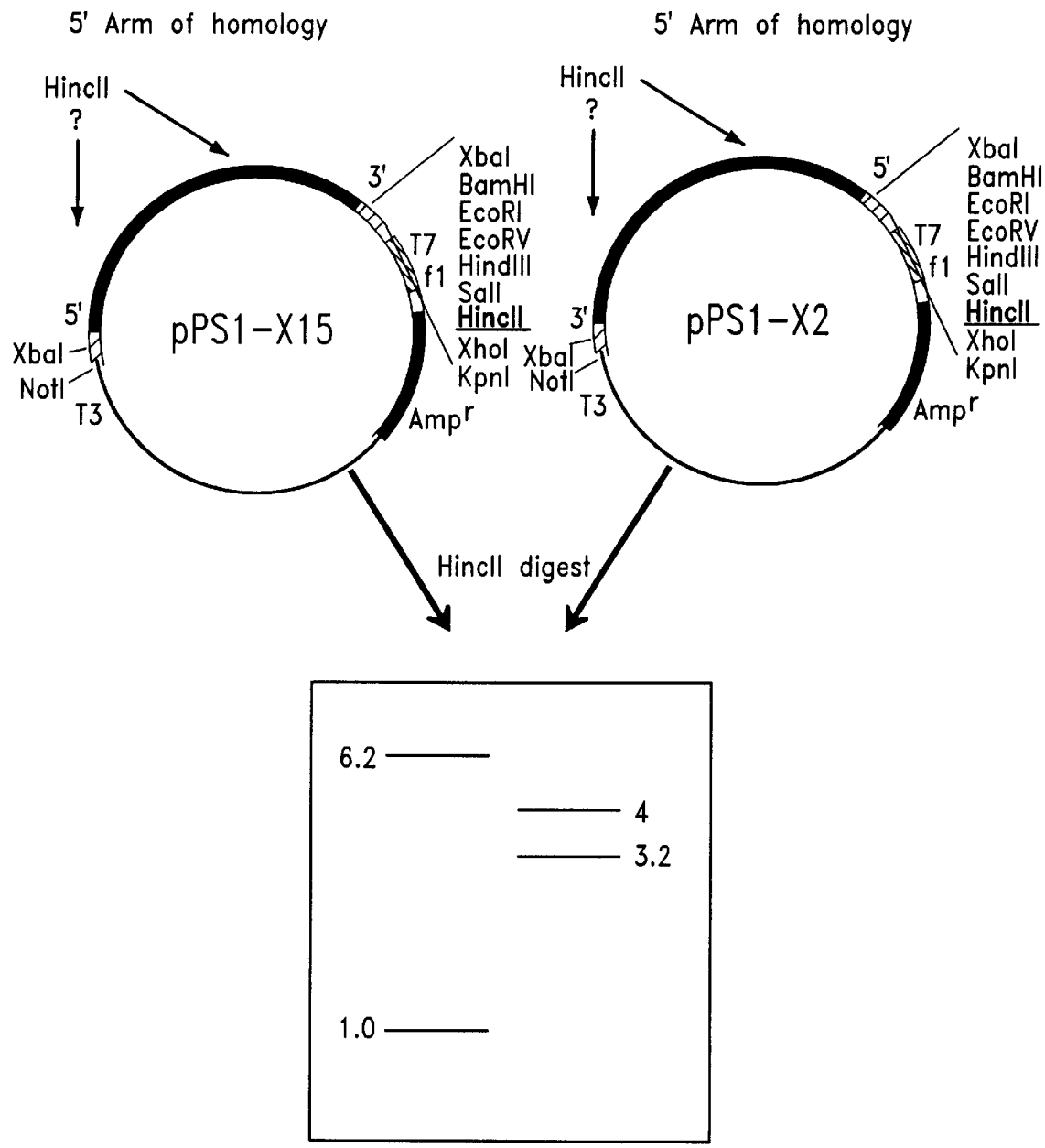
FIG. 11 is a schematic diagram illustrating the restriction mapping of the 5' Arm of Homology from plasmids pPS1-X15 and pPS1-X2.
Figure 11:

(c) Restriction mapping arms of homology. Further restriction enzyme mapping was performed on the pPS1-X15 and pPS1-X2. As an example, each of the two plasmids were digested with the enzyme HincII, resolved on an agarose gel, and visualized with ethidium bromide. Because a HincII site is known to exist the pBlueScript® SK+ plasmid backbone within the multiple cloning site region near the T7 promoter relative to the insert position, it was possible to determine the position of the HincII site in the 4.2 PS-1 fragment by determining the fragment sizes in each of the two digested samples (FIG. 11).

Figure 12:
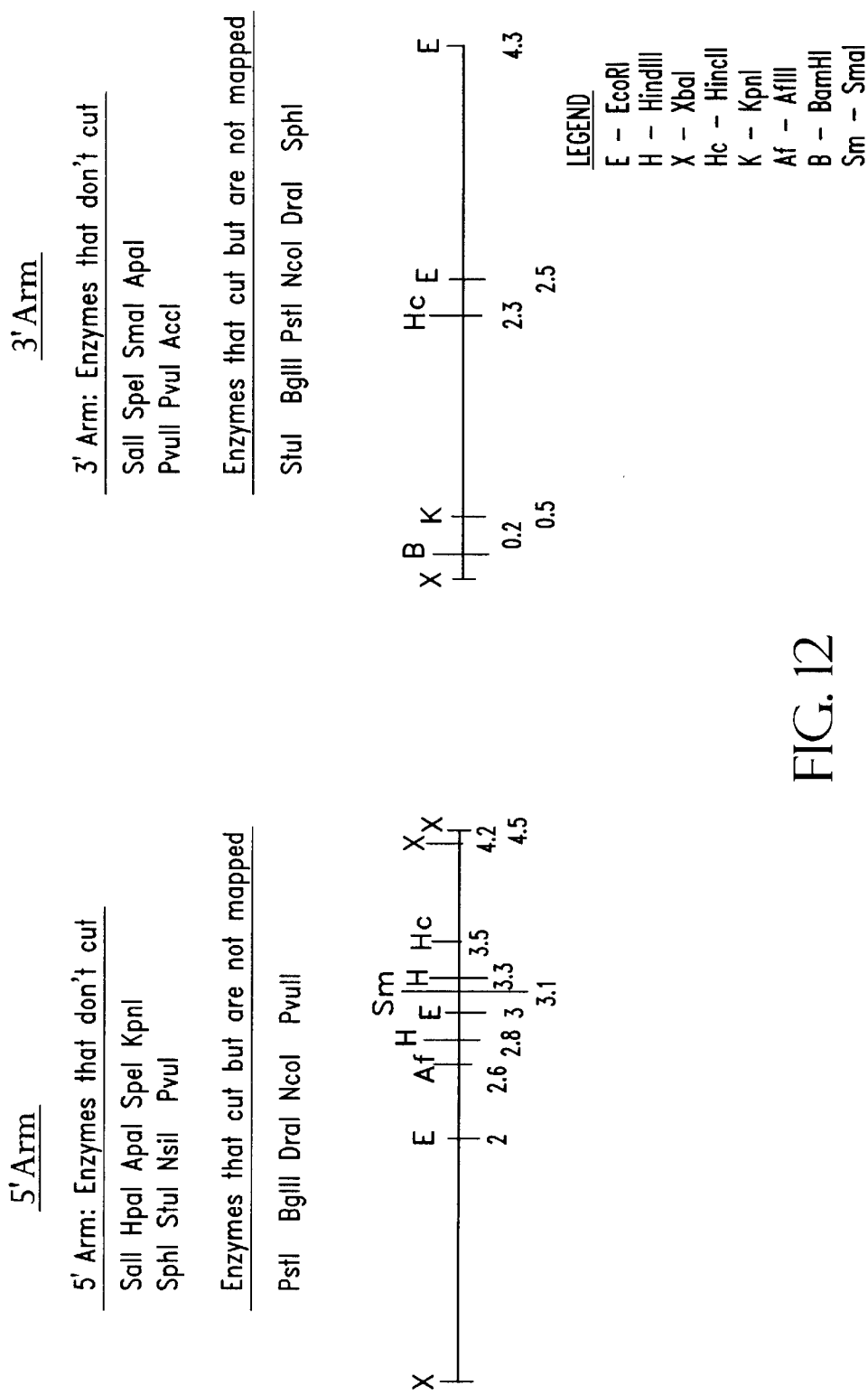
FIG. 12 is a pair of restriction maps for the PS1 3' and 5' arms of homology.

Positions of restriction enzymes sites that occurred once or twice in the 4.2 kb PS-1 fragment were determined by the above method. If more than two sites of a given enzyme were present, it became necessary to determine the relative positions by double-digesting each of the two plasmids with the enzyme in question as well as an additional enzyme which cut at sites capable of resolving ambiguities. In many cases, enzymes that cut more than twice were not resolved in this way but simply noted as having multiples sites in the 4.2 kb PS-1 fragment. The list of additional enzymes used to characterized this region include: AccI, ApaI, BamHI, EcoRV, HincII, HpaI, KpnI, NsiI, PstI, SalI, SmaI, SpeI, and XhoI. A summary of this data is illustrated in FIG. 12. The same procedures were used to create a restriction enzyme map for the pPS1-XH16 (FIG. 12).

Figure 13:
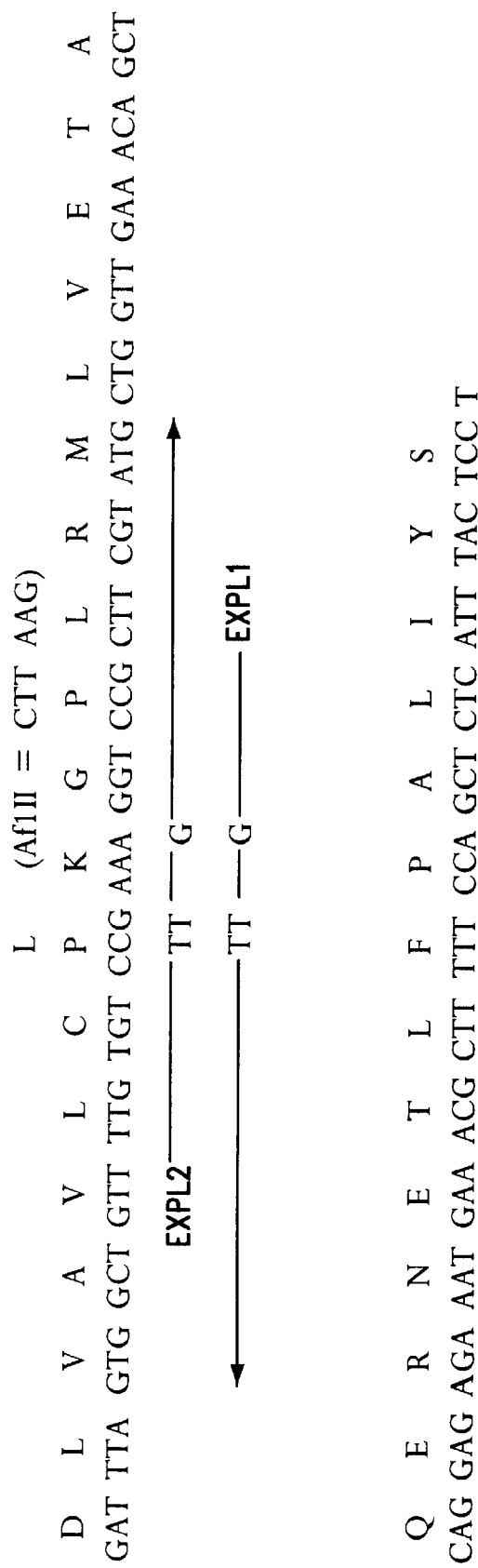
FIG. 13 is a partial sequence of exon 8 of PS-1 illustrating the base changes to effect the P264L mutation and the addition of the AflIII restriction endonuclease site of this invention.

(d) Mutagenesis of the 3' arm of homology. A total of 3 base pair changes were introduced into the exon 8 region using a PCR strategy (for summary of changes, see FIG. 13) The P264L mutation, and an AflII site were introduced. Ten ng of pPS1-XB1 were included into each of two PCR reactions. The first reaction contained the primers EXPL2 (TTG TGT CTT AAG GGT CCG CTT CGT ATG; SEQ ID NO. 11) and T7 (Stratagene Cloning Systems, La Jolla, Calif.). This generated a 220 bp band that encompassed the 3' end of exon 8 and clone PS1-XB 1. This fragment also included the P264L mutation and a novel AflII site that resulted as part of the P264L change.

Figure 14:
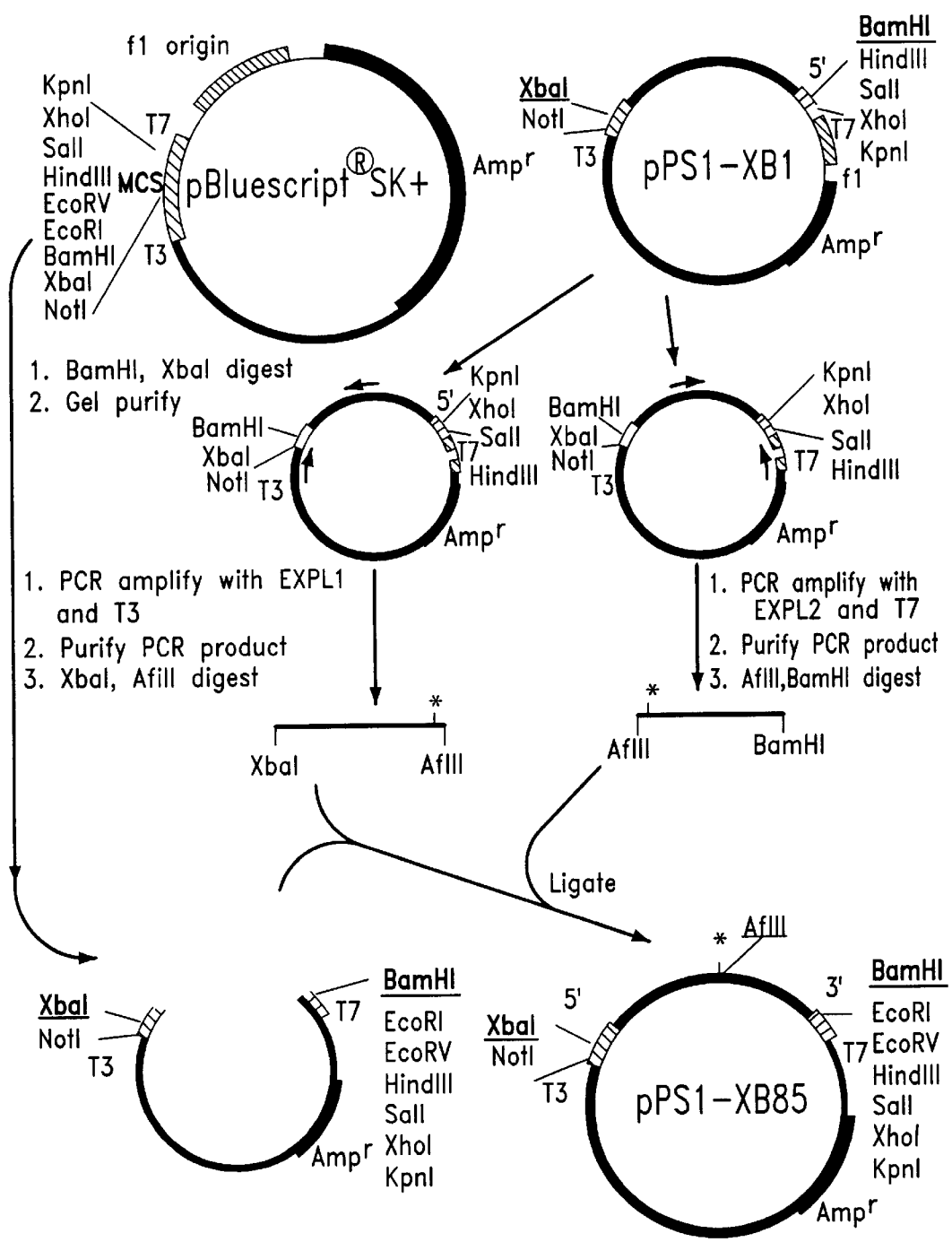
FIG. 14 is a schematic diagram illustrating the construction of plasmid pPS1-XB85.

The second PCR reaction used the primers EXPL1 (CGG ACC CTT AAG ACA CAA AAC AGC CAC; SEQ ID NO. 12) and T3 (Stratagene Cloning Systems, La Jolla, Calif.). This generated a 137 bp fragment that encompassed the 5' end of exon 8 and PS1-XB1. This fragment also included the P264L change and an AflII site (FIG. 14).

The product of the first reaction was purified using Magic™ PCR Preps DNA Purification System (Promega Corporation, Madison, Wis.) and digested with BamHI and AflII in order to liberate the restriction sites at its ends. Similarly, the product of the second reaction was purified and digested with AflII and XbaI. These two fragments, as well as XbaI and BamHI digested pBlueScript® SK+ were ligated together and transformed into HB101 competent *E. coli* cells. The DNA was isolated and analyzed from the ampicillin resistant colonies. The clone bearing a recombinant plasmid in which the two PCR fragments had joined together at their AflII site and inserted into the BamHI and XbaI sites of pBlueScript® SK+ was called pPS1-XB85 (FIG. 14). To confirm the sequences of the mutagenized exon 8, direct nucleotide sequencing (Sanger, *Proc. Natl. Acad Sci. USA* 74: 5463–5467 (1977)) was performed using T3 and T7 sequencing primers (Stratagene® Inc., LaJolla, Calif.) and Sequenase Version 2.0 DNA Sequencing Kit (United States Biochemical, Cleveland, Ohio).

Figure 15:
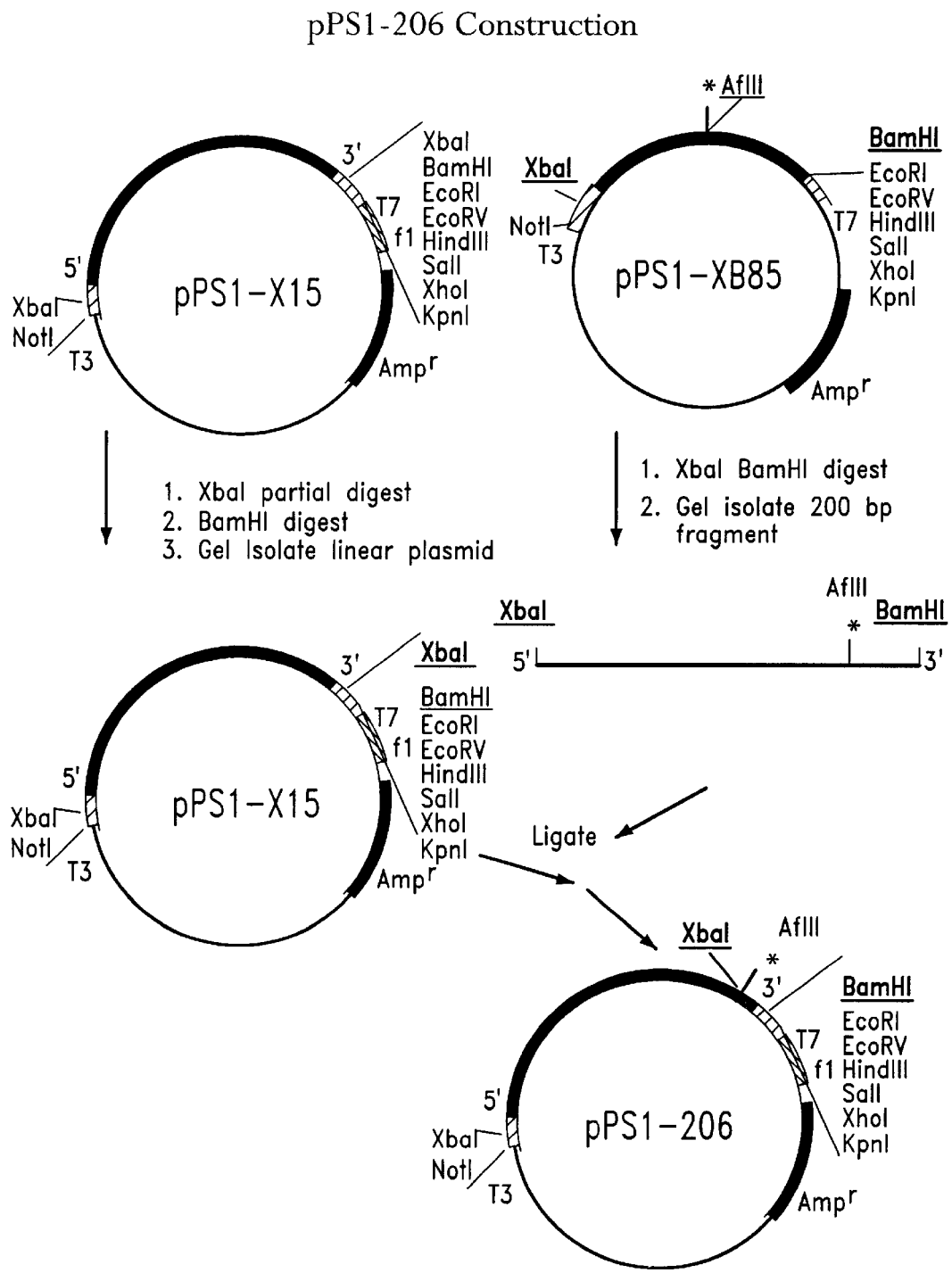
FIG. 15 is a schematic diagram illustrating the construction of plasmid pPS1-206.

The 5' arm of homology was assembled in pBlueScript® SK+ through several cloning steps. First, pPS1-XB 15 was partially digested with XbaI so that only one XbaI site was cut. The resulting DNA was then digested with BamHI and gel purified (FIG. 15).

The mutated insert in pPS1-XB85 was released by digesting it with XbaI and BamHI and gel purifying the resulting mutated insert. The 200 bp XbaI-BamHI fragment was ligated into the linearized pPS1-X15 and recombinant plasmids were screened for the proper orientation of the insert by means of an AflII digest. The correctly oriented plasmid yielded 1.9 kb and 5.8 kb fragments. This plasmid was designated "pPS1-206".

Figure 16:
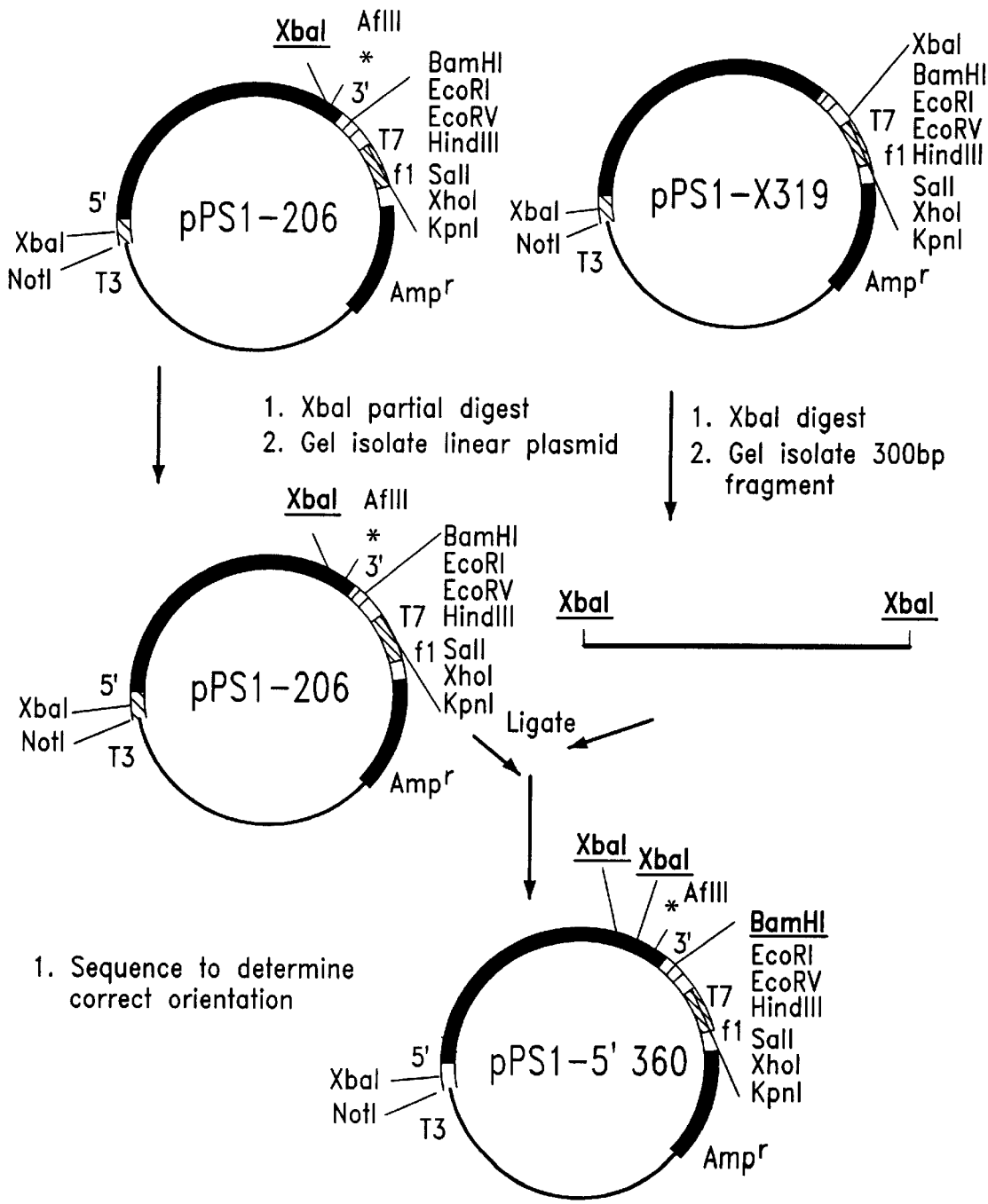
FIG. 16 is a schematic diagram illustrating the construction of plasmid pPS1-360.

To insert the small 300 bp XbaI fragment 5' relative to the mutated 200 bp XbaI-BamHI fragment, pPS1-206 was linearized by a partial XbaI digest (FIG. 16). The XbaI fragment from pPS1-X319 was isolated and cloned into the linearized pPS1-206 DNA. Orientation of the 300 bp XbaI fragment was determined by sequencing the recombinant clone as well as λPS1-20 with primer EX8PL1 using the Thermo Sequenase radiolabeled terminator cycle sequencing kit (Amersharn Life Science Inc., Cleveland, Ohio). A plasmid clone that shared sequence identity with λPS1-20 beyond the XbaI site had the 300 bp XbaI fragment inserted in the proper orientation. This plasmid, which contained the assembled 5' arm, was designated "pPS1-5'360" (FIG. 16).

Figure 17:
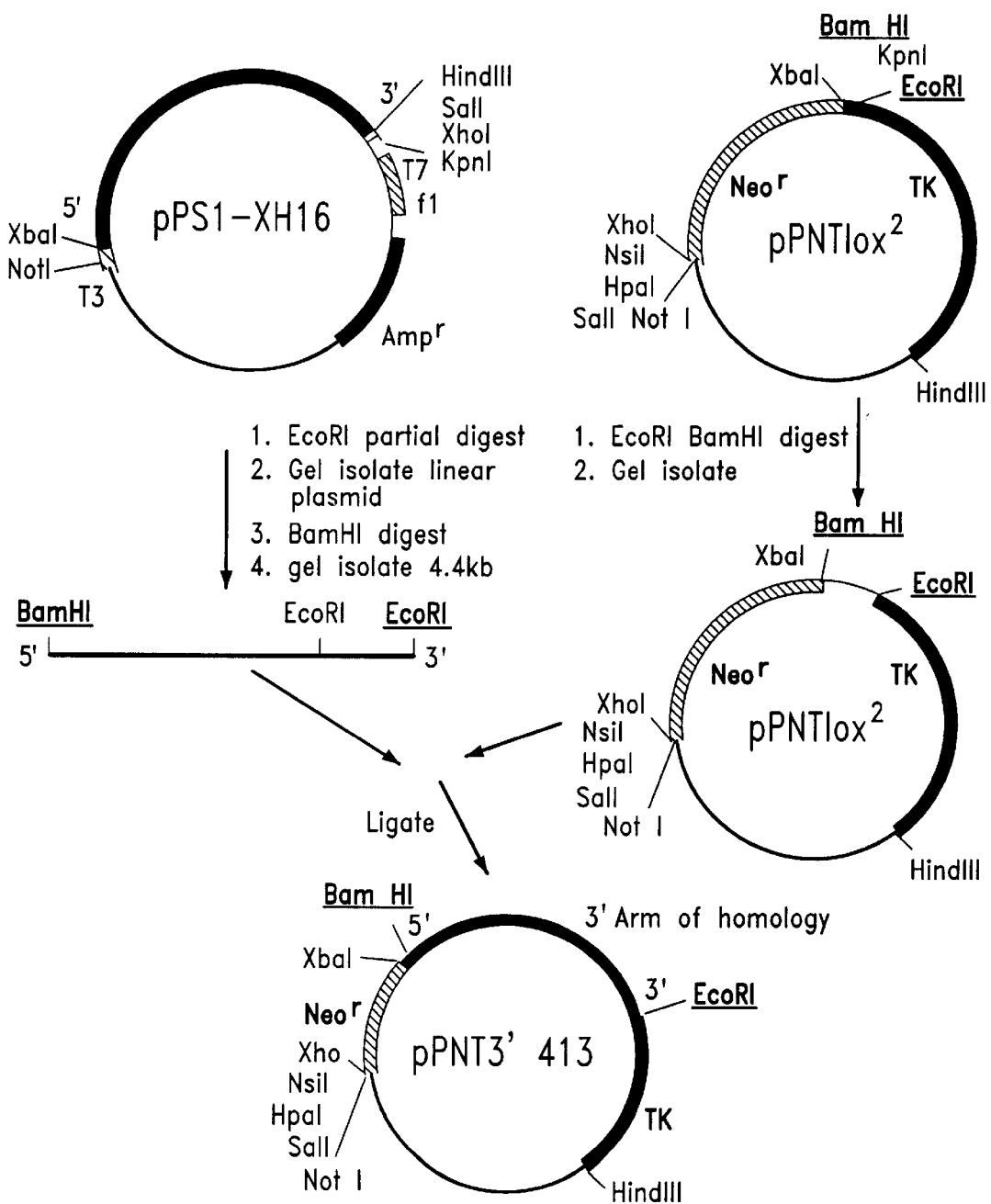
FIG. 17 is a schematic diagram illustrating the construction of plasmid pPNT3'413.

(e) Assembling the targeting vector pPS-1-8-TV. The plasmid pPNTlox$^2$ was prepared for receiving the 3' arm of homology by first digesting plasmid DNA with EcoRI and BamHI and gel isolating the linear plasmid (FIG. 17). In parallel, the 3' arm was prepared by partially digesting pPS1-XH16 with EcoRI and isolating the linear form. This fragment was then digested with BamHI and the 4.1 bp fragment gel isolated. The 3' arm was ligated to pPNTlox$^2$. The resulting plasmid was designated "pPNT3'-413".

Figure 18:
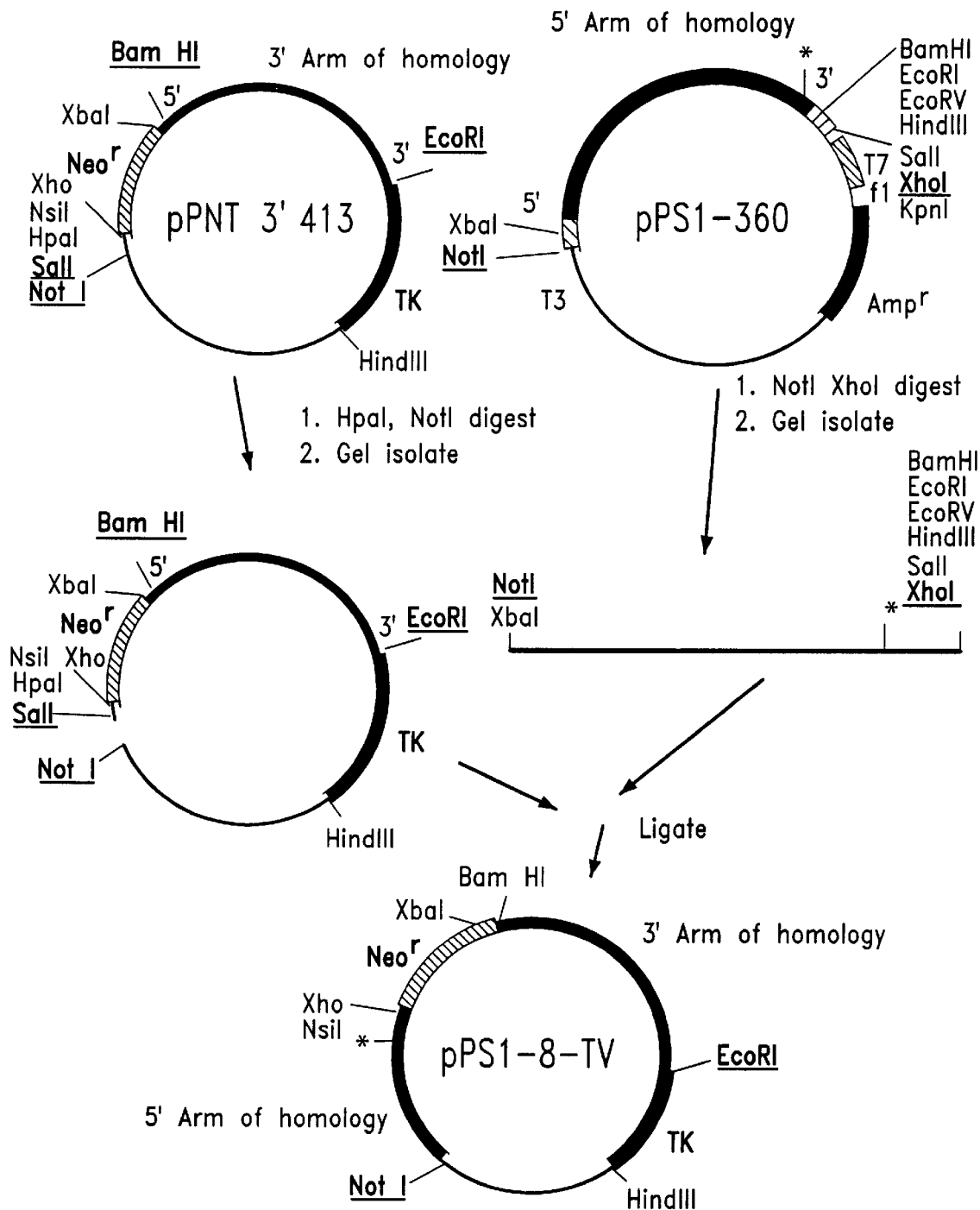
FIG. 18 is a schematic diagram illustrating the construction of plasmid pPS1-8-TV.

The 5' arm was inserted into pPNT3'413 to give the final plasmid pPS1-8-TV. The 5' arm was liberated from plasmid DNA by first digesting with XhoI and NotI. In parallel, pPNT3'413 was prepared by double digesting with NotI and SalI. The two fragments of DNA were ligated and transformed into competent WM 1100 *E. coli* cells (FIG. 18).

Example 3

Mutagenesis of the Mouse PS-1 Gene in ES cells.

(a) Cells. The R1 line of ES cells derived from 129/Svx 129/Sv-CP F1 hybrid mice (Nagy, et al., *Proc. Natl. Acad Sci. USA* 90: 8424–8428 (1993)) and obtained from Dr. Janet Rossant (Mt. Sinai Hospital, Toronto, Ontario, Canada) was utilized. These cells were grown in ES cell medium consisting of Dulbecco's Modification of Eagle's Medium (with L-glutamine and 4500 mg/L glucose; Mediatech Inc., Herndon, Va.) supplemented with 20% fetal bovine serum (FBS; Hyclone Laboratories Inc., Logan, Utah; cat. #A-1115; Lot #11152154), 0.1 mM non-essential amino acids (Mediatech 25-025-L1), 2 mM L-glutamine (Mediatech 25-005-L1), $10^{-6}$ M β-mercaptoethanol (Gibco 21985-023) 1 mM sodium pyruvate (Mediatech 25-000-L1), 1× concentration of a penicillin streptomycin solution (Mediatech 30-001-L1) and 1000 U/ml of leukemia inhibitory factor (Gibco BRL 13275-029). The cells were grown on tissue culture plastic that had been briefly treated with a solution of 0.1% gelatin (Sigma G9391).

The cultures were passed every 48 hours or when the cells became about 80% confluent. For passage, the cells were first washed with phosphate buffered saline (without $Ca^{2+}$ and $Mg^{2+}$) and then treated with a trypsin/EDTA solution (0.05% trypsin, 0.02% EDTA in PBS without $Ca^{2+}$ and $Mg^{2+}$). After all of the cells were in suspension, the trypsin digestion was stopped by the addition of tissue culture medium. The cells were collected by centrifugation, resuspended in 5 ml of tissue culture medium and a 1 ml aliquot of the cell suspension was used to start a new plate of the same size.

(b) DNA transfection of ES cells. pPS1-8-TV DNA (400 μg) was prepared for electroporation by digesting it with NotI in a 1 ml reaction volume. The DNA was then precipitated by the addition of ethanol, washed with 70% ethanol and resuspended in 500 μl of sterile water.

The NotI-linearized pPS1-8-TV DNA was electroporated into ES cells using a Bio-Rad Gene Pulser® System (Bio-Rad Laboratories, Hercules, Calif.). In each of 10 electroporation cuvettes, 40 μg of DNA was electroporated into 2.5×10$^6$ cells suspended in ES cell culture medium. The electroporation conditions were 250V and 500 μF which typically result in time constants ranging between 6.0–6.1 seconds. After electroporation the cells were incubated for 20 minutes at room temperature in the electroporation cuvettes. All the electroporated cells were then pooled and distributed equally onto 10 gelatinized plates. After 24 hours the plates were aspirated and fresh ES cell medium was added. The next day, the medium in 9 plates was replaced with ES cell medium supplemented with 150 μg/mL of G418 (Gibco) and 0.2 μM gancyclovir (Syntex) while one plate received medium supplemented only with 150 μg/mL of G418. After an additional 8 days, resulting individual ES cell colonies were picked off of the plates and separately expanded in a well of 24 well plates as described by Wurst et al., pp 33–61 in *Gene Targeting* Vol. 126 (1993), Edited by A. L. Joyner, IRL Press, Oxford University Press, Oxford, England. Comparison of the number of colonies that grew on the plates supplemented with G418 and gancyclovir versus the number that grew with only G418 supplementation was used to determine the efficiency of negative selection.

(c) Analyses of the ES cell transformants. When the cell culture in each well of the 24-well plates became approximately 80% confluent, it was washed and the cells were dispersed with two drops of trypsin-EDTA. Trypsinization was stopped by the addition of 1 ml of ES cell medium. An aliquot (0.5 mL) of this suspension was transferred to each of two wells of separate 24-well plates. After the cells had grown to near confluence, one of the plates was used for cryopreservation of the cell line while the other was used as a source of DNA for each of the clones.

For cryopreservation, the cells in a 24-well plate were first chilled by placing the plate on ice. The medium was then replaced with fresh ES cell medium supplemented with 10% DMSO and 25% FBS and the plate was cooled at approximately 0.5° C./min by insulating the plate in a styrofoam box and placing it in a −70° C. freezer.

To isolate the DNA from the clones on the other plate, the medium in each well was replaced with 500 μl of digestion buffer (100 mM Tris-HCl, pH8.5, 5 mM EDTA, 0.2% SDS, 200 mM NaCl, 100 μg/ml proteinase K). After overnight incubation at 37° C., 500 μl of isopropanol was added to each well and the plate was agitated for 15 minutes on an orbital shaker. The supernatant was aspirated and replaced with 500 μl of 70% ethanol and the plate was shaken for an additional 15 minutes. The DNA precipitate was picked out of the well and dissolved in 50 μl of TE solution (10 mM Tris-HCl pH 7.5, 1 mM EDTA).

The primary analysis for mutagenesis of the mouse PS-1 gene involved a Southern hybridization screen of ApaI digested ES cell DNA. The probe for this analysis was derived from the 3' end of our cloned PS-1 region outside of the 3' arm of homology (FIG. 19d). It was prepared by first isolating the 6 kb XbaI fragment corresponding to the 3' end of λPS1-6 (FIG. 2) and subcloning it into XbaI digested pBlueScript® SK+. A further digest of this subclone, called pPS1-X6 with XhoI (an internal site) and HindIII (from the pBlueScript® SK+ polylinker) yielded the 1000 bp probe.

Figure 19:
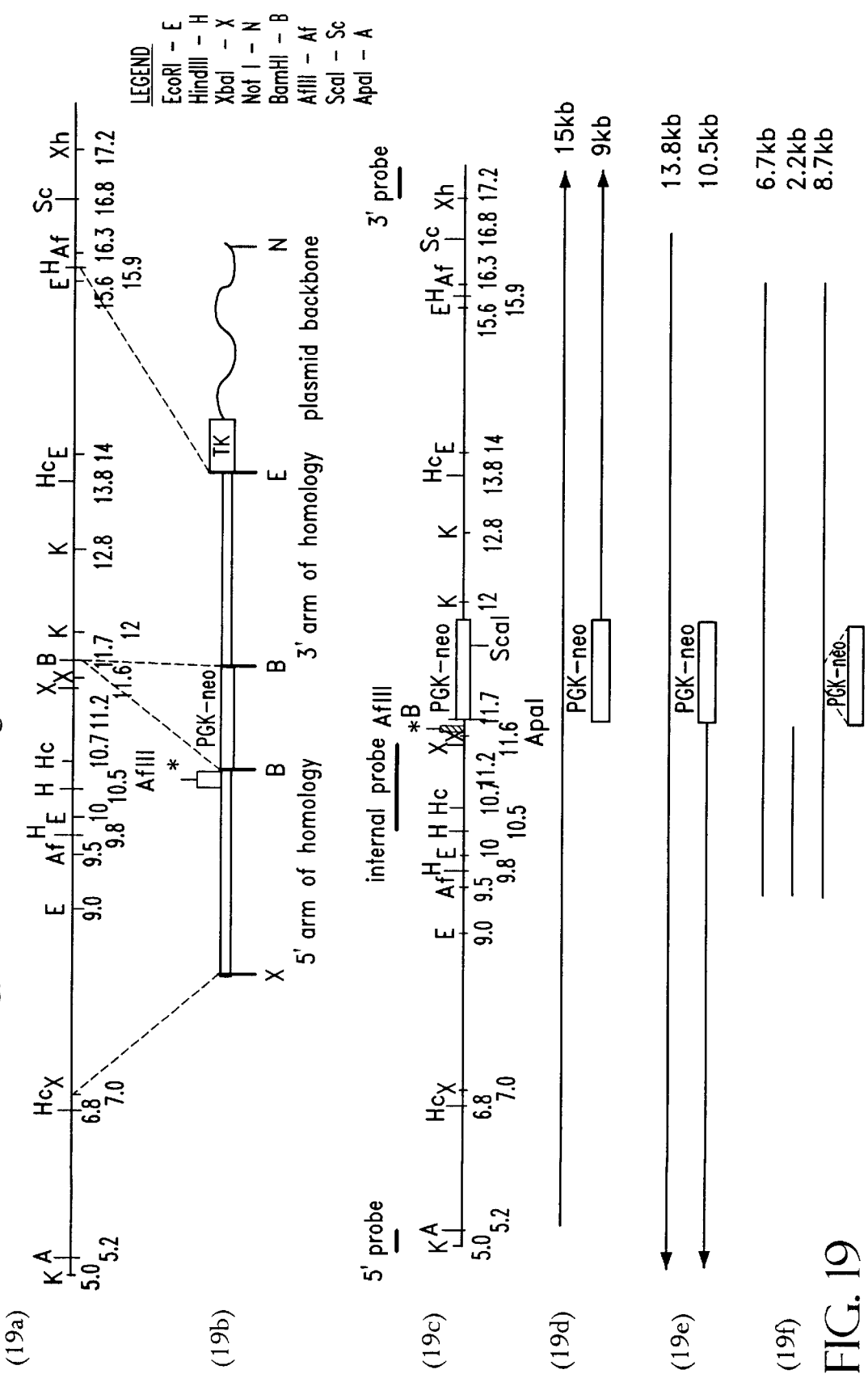
FIG. 19 is a schematic diagram illustrating the strategy to detect homologous recombination within mouse PS1. Letter abbreviations for restriction endonucleases are as follows: E, EcoRI; X, XbaI; N NotI; H, HindIII; B, BamHI; A, ApaI; Af, AflII; Sc, ScaI.

For the Southern hybridization screen, an aliquot (10 μl) of each ES cell clone DNA was digested with ApaI, resolved on a 0.8% agarose gel, and transferred to a GeneScreen Plus® membrane. The probe was labelled with $^{32}$P-dCTP by random priming and hybridized overnight to the membrane at 58° C. (Church et al., *Proc. Natl. Acad. Sci.* 81: 1991–1995 (1984)). An ES cell line in which the PS-1 gene has successfully undergone homologous recombination yields 9 and 15 kb ApaI fragments in this assay (FIG. 19).

This is because homologous recombination advantageously introduces a novel ApaI site into the region where the neo$^r$ cassette is incorporated. The 15 kb band represents the unaltered cellular copy of PS-1 while the 9 kb band is derived from the PS-1 copy in which the novel ApaI site results in a shorter fragment. In this first screen, 8 cell lines were identified as potential targeted cell lines out of 260 cell lines analyzed.

All cell lines scored as putative homologous recombinants by the primary screen were then further screened using a 500 bp KpnI-ApaI fragment isolated from a 5.5 kb 5' XbaI fragment from λPS1-20 on ScaI digested ES cell DNA. In this case, the normal PS-1 gene yielded a 13.8 kb fragment and the mutant PS-1 gene a 10.5 kb fragment (FIG. 19e). Of the 8 cell lines examined in this screen, 4 were shown to have undergone homologous recombination at their 5' end.

Cell lines that were identified as having undergone homologous recombination by both screens were considered to have undergone bonafide homologous recombination (as opposed to homologous insertion which would give positive results for only 1 of the 2 preceding screens). However, depending on where crossover takes place when the 5' arm recombines the mutations that we included in this arm may or may not have been incorporated into cellular DNA as a result of proper homologous recombination (FIG. 1). A further Southern hybridization screen aimed at detecting the novel AflIII site created as a result of the P264L mutation was therefore implemented. For this, a 1.2 kb HindIII-XbaI fragment isolated from pPS1-X15 as a probe on AflII digested DNA was utilized. An unaltered PS-1 gene yielded a 6.7 kb band (FIG. 19f). A PS-1 gene in which proper homologous recombination has taken place, but which lacks the planned mutations yields a 8.7 kb band while the inclusion of the planned mutations yields a 2.2 kb band. Of the 4 bonafide homologous recombinant cell lines examined, all 4 were shown to have incorporated the novel AflII site near the planned mutations.

The mutagenized form of the PS-1 gene described here has been called pS1$^{nP264L}$ as opposed to the normal PS-1 gene termed PS1$^+$. The four ES cell lines bearing one copy of PS-1$^{nP264L}$ have been called, PS1-87, PS1-175, PS1-176, and PS1-243. Three of these lines thawed, cell numbers expanded, and used to establish PS-1 mutant mice.

Example 4

Establishment of PS-1 Mutant Mice

PS-1 mutant ES cells were used to make chimeric mice by aggregating the mutant ES cells to E2.5 embryos and transferring the aggregated embryos to pseudopregnant females. (Wood, et al., *Nature* 365: 87–89 (1993)). ES cells were prepared for aggregation by limited trypsinization to produce clumps that average 10–15 cells. E2.5 embryos were collected from superovulated CD-1 female mice by oviduct flushing as described by Hogan, et al., *Manipulating the Mouse Embryo: A Laboratory Manual*, (1986) Cold Spring Harbor Laboratory, Cold Spring Harbor, N.Y.). The zona pelucida was removed from the embryos using acidic Tyrode's solution (Sigma Chemical Co., St. Louis, Mo.). Aggregation wells were created by pressing a blunt metal instrument (a darning needle) into tissue culture plastic. Embryos were then placed in a well together with a clump of approximately 10–15 ES cells in a small drop (approximately 20 μl) of M16 medium (Sigma Chemical Co., St. Louis, Mo.) under mineral oil. After an overnight incubation (37° C., 100% humidity, 5% CO$_2$ in air) the aggregate embryos were transferred to the uterine horns of a pseudopregnant female (Hogan et al., 1986 supra). Contribution of the ES cells to the offspring was scored by the appearance of pigmented coat color. Positive mice are termed chimeric founders. Germline contribution by the ES cells was scored by the appearance of pigmented offspring from a cross between the chimeric founders and CD-1 females.

Of 3 mutant PS-1 ES cell lines used in embryo aggregations, one produced a germline chimera:

TABLE 1

| Clone | Number of Embryo Aggregation | Number of Chimeric Founders | Number of Germline Chimeras |
|---|---|---|---|
| PSI-175 | 400 | 5 | 1 |
| PSI-176 | 75 | 4 | 0 |
| PSI-243 | 120 | 0 | 0 |

The germline chimera was then used to establish lines of mice carfying PS-1$^{nP264L}$. The presence of the mutant PS-1 allele in the pigmented offspring was determined using a PCR strategy aimed at detecting the neo$^r$ cassette, following substantially the same procedure as set forth in Example 1. PCR primers were as follows: neo28 (GGA TTG CAC GCA GGT TCT CC; SEQ ID NO. 13); and neo445 (CCG GCT TCC ATC CGA GTA CG; SEQ ID NO.14). The genomic DNA was prepared from a tail sample (Hogan, 1986 supra). Of the four pigmented offspring, one female mouse was heterozygous for PS-1$^{nP264L}$ (PS-1$^{nP264L}$/PS-1$^+$), i.e., this mouse was positive for the neo$^r$ cassette based upon the foregoing PCR strategy. Subsequent generational offspring which are also heterozygous for PS-1$^{nP264L}$ have been developed by mating of this 10 female with wild-type males.

Mice heterozygous for PS-1$^{nP264L}$ (PS-1$^{nP264L}$/PS-1$^+$) were genotyped using a PCR-based method. The presence of the wild-type allele for murine PS-1 was scored using the following primers: X8F (CCC GTG GAG GAG GTC AGA AGT CAG; SEQ ID NO. 15) and X8R (TTA CGG GTT GAG CCA TGA ATG; SEQ ID NO. 16). Scoring with these primers yields a 142 bp fragment (data not shown). The presence of the mutant allele was scored using the primers neo28 and neo445, which yields a 417 bp fragment. Thus, mice which are heterozygous for the mutation yield both bands; mice which are homozygous for the mutation yield only the 417 bp band; and mice that are homozygous for the wild-type allele yield only the 142 bp band. Tissue samples were derived from animal tails, and the PCR procedures of Example 1 were utilized for such scoring.

Mice homozygous for the pS-1$^{nP264L}$ allele (i.e., pS-1$^{nP264L}$/PS-1$^{nP264L}$) were generated by cross breeding of heterozygous mice (PS-1$^{nP264L}$/PS-1$^+$) with mice which are homozygous for a humanized APP gene (as disclosed in PCT Publication Number WO96/34097, published Oct. 31, 1996; incorporated herein fully by reference). The resulting generational offspring were then determined to be heterozygous for both the PS-1$^{nP264L}$ allele and heterozygous for the humanized APP gene (data not shown); these generational offspring were then utilized for cross-breeding, with resulting generational offspring determined (using the PCR procedure outlined above) to be homozygous for the PS-1$^{nP264L}$ allele, as well heterozygous for the humanized APP gene (generational offspring from this liter were also found to be heterozygous for the PS-1$^{nP264L}$ allele/homozygous for the humanized APP gene; and heterozygous for the pS-1$^{nP264L}$ allele/heterozygous for the humanized APP gene—due to the limited number of pups obtained from this liter, double homozygotes were not found).

Mice homozygous for the pS-1$^{nP264L}$ allele were also generated by cross-breeding of heterozygous mice (PS-1$^{n1264L}$/PS-1$^+$). In one set of matings, 6 homozygotes were found amongst 27 offspring, which is well within the expected 25% recovery of homozygotes from a heterozygous cross.

Accordingly, and based upon the various breeding approaches disclosed above, substantially normal viability and embryonic survival of the animals is evident.

What is claimed is:

1. A gene-targeted mouse heterozygous for human presenilin-1 (PS-1) mutation, said mouse comprising, in its genome, a DNA sequence encoding a functionally active PS-1 protein comprising the human P264L mutation, wherein said PS-1 protein is expressed, and wherein the Aβ42 protein level is elevated relative to the Aβ42 protein level in a wild-type mouse.

2. The mouse of claim 1, wherein said mutation protein encoding sequence encodes a guanosine residue at codon 265 of the mouse PS-1 encoding sequence.

3. A generational offspring of the mouse of claim 1, wherein said offspring comprises, in its genome, a DNA sequence encoding a functionally active PS-1 protein comprising the human P264L mutation, wherein said PS-1 protein is expressed, and wherein the Aβ42 protein level is elevated relative to the Aβ42 protein a wild-type mouse.

4. A gene-targeted mouse homozygous for human presenilin-1 (PS-1) mutation, said mouse comprising, in its genome, a DNA sequence encoding a functionally active PS-1 protein comprising the human P264L mutation, wherein said PS-1 protein is expressed, and wherein the Aβ42 protein level is elevated relative to the Aβ42 protein level in a wild-type mouse.

5. The mouse of claim 4, wherein said mutation protein encoding sequence encodes a guanosine residue at codon 265 of the mouse PS-1 encoding sequence.

6. A generational offspring of the mouse of claim 4, wherein said offspring comprises, in its genome, a DNA sequence encoding a functionally active PS-1 protein comprising the human P264L mutation, wherein said PS-1 protein is expressed, and wherein the Aβ42 protein level is elevated relative to the Aβ42 protein a wild-type mouse.

7. A method for screening a chemical compound for the ability to decrease in vivo levels of the Aβ42 peptide, said method comprising the steps of:
  (a) administering said chemical compound to the mouse of claim 6;
  (b) obtaining a tissue sample from said mouse; and
  (c) measuring the amount of Aβ42 in said issue sample, wherein a decrease in the amount of Aβ42 peptide in said issue sample compared to the amount of Aβ42 peptide in a mouse to which said chemical compound was not administered is indicative of a chemical compound that has the ability to decrease in vivo levels of said Aβ42 peptide.

8. The method of claim 7 wherein said tissue sample is selected from the group consisting of: brain tissue, non-brain tissue and body fluids.

9. A method for screening a chemical compound for the ability to decrease in vivo levels of the Aβ42 peptide, said method comprising the steps of:
  (a) administering said chemical compound to the mouse of claim 4;
  (b) obtaining a tissue sample from said mouse; and
  (c) measuring the amount of Aβ42 in said tissue sample, wherein a decrease in the amount of Aβ42 peptide in said tissue sample compared to the amount of Aβ42 peptide in a mouse to which said chemical compound was not administered is indicative of a chemical compound that has the ability to decrease in vivo levels of said Aβ42 peptide.

10. The method of claim 9 wherein said tissue sample is selected from the group consisting of: brain tissue, non-brain tissue and body fluids.

* * * * *

UNITED STATES PATENT AND TRADEMARK OFFICE
CERTIFICATE OF CORRECTION

PATENT NO. : 6,284,944 B1
DATED : September 4, 2001
INVENTOR(S) : Richard W. Scott, Andrew G. Geaume and Karen Dorfman It is certified that error appears in the above-identified patent and that said Letters Patent is hereby corrected as shown below:

Column 3,
Line 28, please delete "Duffet al." and insert -- Duff et al. -- therefor.

Column 4,
Line 21, please delete "(1C)" and insert -- (1c) -- therefor.

Column 5,
Line 5, please delete "Scal;" and insert -- Scal. -- therefor.

Column 9,
Line 5, please delete "incorporated" and insert -- incorporate -- therefor.
Line 59, please delete "have".

Column 11,
Line 49, please delete "Ecrol" and insert -- EcoRl -- therefor.

Column 12,
Line 12, please delete "PlasmidpPNTlox$^2$" and insert -- Plasmid pPNTlox$^2$ -- therefor.

Column 18,
Line 35, please delete "10".
Line 64, please delete "liter" and insert -- litter -- therefor.

Column 19,
Line 1, please delete "liter" and insert -- litter -- therefor.

Column 25,
Lines 37 and 53, please insert -- level in -- between "protein" and "a".

UNITED STATES PATENT AND TRADEMARK OFFICE
CERTIFICATE OF CORRECTION

PATENT NO.    : 6,284,944 B1
DATED         : September 4, 2001
INVENTOR(S)   : Richard W. Scott, Andrew G. Geaume and Karen Dorfman It is certified that error appears in the above-identified patent and that said Letters Patent is hereby corrected as shown below:

Column 26,
Lines 27 and 29, please delete "issue" and insert -- tissue -- therefor.

Signed and Sealed this

Ninth Day of August, 2005

JON W. DUDAS
*Director of the United States Patent and Trademark Office*

```
                       SEQUENCE LISTING (1) GENERAL INFORMATION:

(iii) NUMBER OF SEQUENCES:  16

(2) INFORMATION FOR SEQ ID NO: 1:

(i) SEQUENCE CHARACTERISTICS:
         (A) LENGTH:21 base pairs
         (B) TYPE:nucleic acid
         (C) STRANDEDNESS:single
         (D) TOPOLOGY:linear (ii) MOLECULE TYPE:Genomic DNA (xi) SEQUENCE DESCRIPTION:  SEQ ID NO: 1:

CTC ATC TTG GCT GTG ATT TCA                                        21

(2) INFORMATION FOR SEQ ID NO: 2:

(i) SEQUENCE CHARACTERISTICS:
         (A) LENGTH:18 base pairs
         (B) TYPE:nucleic acid
         (C) STRANDEDNESS:single
         (D) TOPOLOGY:linear (ii) MOLECULE TYPE:Genomic DNA (xi) SEQUENCE DESCRIPTION:  SEQ ID NO: 2:

GTT GTG TTC CAG TCT CCA                                            18

(2) INFORMATION FOR SEQ ID NO: 3:

(i) SEQUENCE CHARACTERISTICS:
         (A) LENGTH:19 base pairs
         (B) TYPE:nucleic acid
         (C) STRANDEDNESS:single
         (D) TOPOLOGY:linear (ii) MOLECULE TYPE:Genomic DNA (xi) SEQUENCE DESCRIPTION:  SEQ ID NO: 3:

ATT TAG TGG CTG TTT TGT G                                          19

(2) INFORMATION FOR SEQ ID NO: 4:

(i) SEQUENCE CHARACTERISTICS:
         (A) LENGTH:20 base pairs
         (B) TYPE:nucleic acid
         (C) STRANDEDNESS:single
         (D) TOPOLOGY:linear (ii) MOLECULE TYPE:Genomic DNA (xi) SEQUENCE DESCRIPTION:  SEQ ID NO: 4:

AGG AGT AAA TGA GAG CTG GA                                         20

(2) INFORMATION FOR SEQ ID NO: 5:
```

(i) SEQUENCE CHARACTERISTICS:
    (A) LENGTH:21 base pairs
    (B) TYPE:nucleic acid
    (C) STRANDEDNESS:single
    (D) TOPOLOGY:linear (ii) MOLECULE TYPE:Genomic DNA (xi) SEQUENCE DESCRIPTION:  SEQ ID NO: 5:

TGA AAT CAC AGC CAA GAT GAG                                          21

(2) INFORMATION FOR SEQ ID NO: 6:

(i) SEQUENCE CHARACTERISTICS:
        (A) LENGTH:22 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 6:

GCA CTC CTG ATC TGG AAT TTT G                                        22

(2) INFORMATION FOR SEQ ID NO: 7:

(i) SEQUENCE CHARACTERISTICS:
        (A) LENGTH:48 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 7:

GGA AAG AAT GCG GCC GCT GTC GAC GTT AAC ATG CAT ATA ACT TCG TAT      48

(2) INFORMATION FOR SEQ ID NO: 8:

(i) SEQUENCE CHARACTERISTICS:
        (A) LENGTH:47 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 8:

GCT CTC GAG ATA ACT TCG TAT AGC ATA CAT TAT ACG AAG TTA TAT GC       47

(2) INFORMATION FOR SEQ ID NO: 9:

(i) SEQUENCE CHARACTERISTICS:
        (A) LENGTH:33 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 9:

CGT TCT AGA ATA ACT TCG TAT AAT GTA TGC TAT                          33

(2) INFORMATION FOR SEQ ID NO: 10:

(i) SEQUENCE CHARACTERISTICS:
        (A) LENGTH:33 base pairs
        (B) TYPE:nucleic acid
        (C) STRANDEDNESS:single (D) TOPOLOGY:linear (ii) MOLECULE TYPE:Genomic DNA (xi) SEQUENCE DESCRIPTION:  SEQ ID NO: 10:

CGT GGA TCC ATA ACT TCG TAT AGC ATA CAT TAT                                33

(2) INFORMATION FOR SEQ ID NO: 11:

(i) SEQUENCE CHARACTERISTICS:
        (A) LENGTH:27 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 11:

TTG TGT CTT AAG GGT CCG CTT CGT ATG                                        27

(2) INFORMATION FOR SEQ ID NO: 12:

(i) SEQUENCE CHARACTERISTICS:
        (A) LENGTH:27 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 12:

CGG ACC CTT AAG ACA CAA AAC AGC CAC                                        27

(2) INFORMATION FOR SEQ ID NO: 13:

(i) SEQUENCE CHARACTERISTICS:
        (A) LENGTH:20 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 13:

GGA TTG CAC GCA GGT TCT CC                                                 20

(2) INFORMATION FOR SEQ ID NO: 14:

(i) SEQUENCE CHARACTERISTICS:
        (A) LENGTH:20 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION:  SEQ ID NO: 14:

CCG GCT TCC ATC CGA GTA CG                                                 20

(2) INFORMATION FOR SEQ ID NO: 15:

(i) SEQUENCE CHARACTERISTICS:
        (A) LENGTH:24 base pairs
        (B) TYPE:nucleic acid
        (C) STRANDEDNESS:single
        (D) TOPOLOGY:linear (ii) MOLECULE TYPE:Genomic DNA -continued

```
    (xi) SEQUENCE DESCRIPTION: SEQ ID NO: 15:

CCC GTG GAG GAG GTC AGA AGT CAG                                         24

(2) INFORMATION FOR SEQ ID NO: 16:

(i) SEQUENCE CHARACTERISTICS:
        (A) LENGTH:21 base pairs
        (B) TYPE:nucleic acid
        (C) STRANDEDNESS:single
        (D) TOPOLOGY:linear (ii) MOLECULE TYPE:Genomic DNA (xi) SEQUENCE DESCRIPTION: SEQ ID NO: 16:

TTA CGG GTT GAG CCA TGA ATG                                             21
```